(12) United States Patent
Park

(10) Patent No.: US 8,288,542 B2
(45) Date of Patent: Oct. 16, 2012

(54) NOBLE RUTHENIUM-TYPE SENSITIZER AND METHOD OF PREPARING THE SAME

(75) Inventor: Chan-seok Park, HwaSeoung (KR)

(73) Assignee: Dongjin Semichem Co., Ltd., Incheon (KR)

( * ) Notice: Subject to any disclaimer, the term of this patent is extended or adjusted under 35 U.S.C. 154(b) by 397 days.

(21) Appl. No.: 12/527,767

(22) PCT Filed: Feb. 15, 2008

(86) PCT No.: PCT/KR2008/000889
§ 371 (c)(1),
(2), (4) Date: Aug. 19, 2009

(87) PCT Pub. No.: WO2008/102962
PCT Pub. Date: Aug. 28, 2008

(65) Prior Publication Data
US 2010/0071763 A1    Mar. 25, 2010

(30) Foreign Application Priority Data
Feb. 21, 2007  (KR) .................. 10-2007-0017360

(51) Int. Cl.
*C07F 15/00* (2006.01)
*H01L 51/00* (2006.01)

(52) U.S. Cl. ............................. 546/2; 313/498; 313/504
(58) Field of Classification Search ...... 546/2; 313/498, 313/504
See application file for complete search history.

(56) References Cited

U.S. PATENT DOCUMENTS
2003/0062082 A1    4/2003    Miteva et al.

FOREIGN PATENT DOCUMENTS
| EP | 1176618 A1 | 1/2002 |
| EP | 1213776 A2 | 6/2002 |
| JP | 2001-152044 A | 6/2001 |
| JP | 2001-226607 | 4/2003 |

*Primary Examiner* — Charanjit Aulakh
(74) *Attorney, Agent, or Firm* — Lexyoume IP Meister, PLLC.

(57) ABSTRACT

The present invention relates to a ruthenium-type dye and a making method thereof, and more particularly, to a ruthenium-type dye which is used to manufacture a dye-sensitized solar cell, drastically improves a molar extinction coefficient to enhance efficiency of a solar cell with only a small amount of a dye and oxide semiconductor particles, allows a thin film solar cell element to be manufactured without difficulty and sharply reduces manufacturing costs of a solar cell, and a making method thereof.

16 Claims, 2 Drawing Sheets

[Fig. 1]
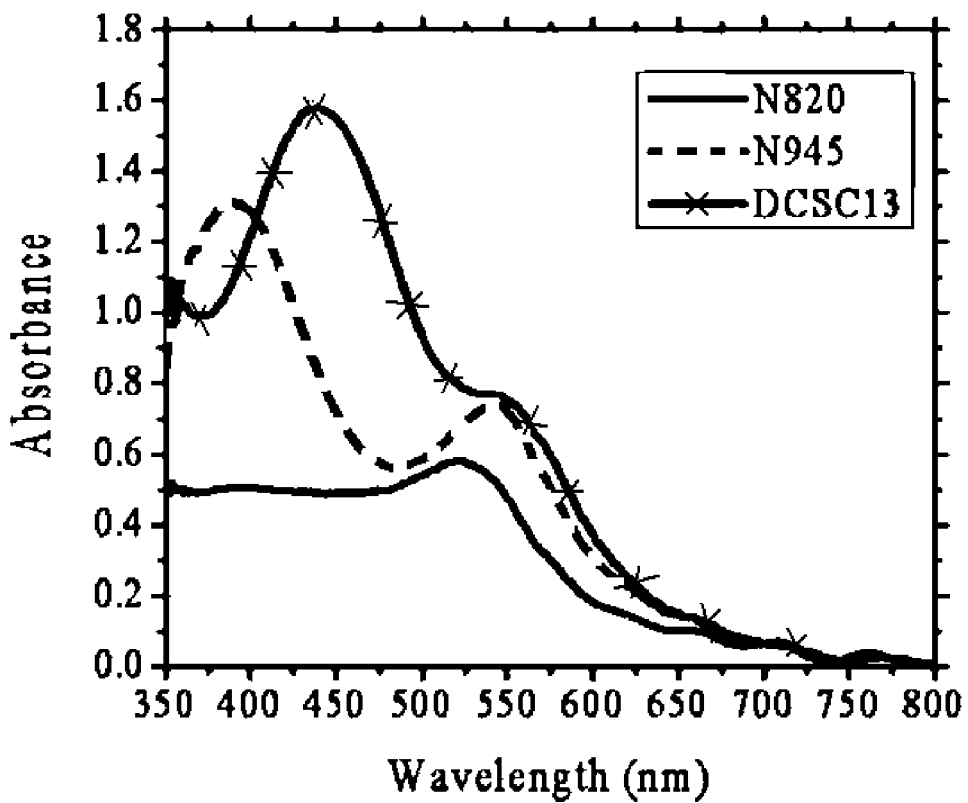
[Fig. 2]
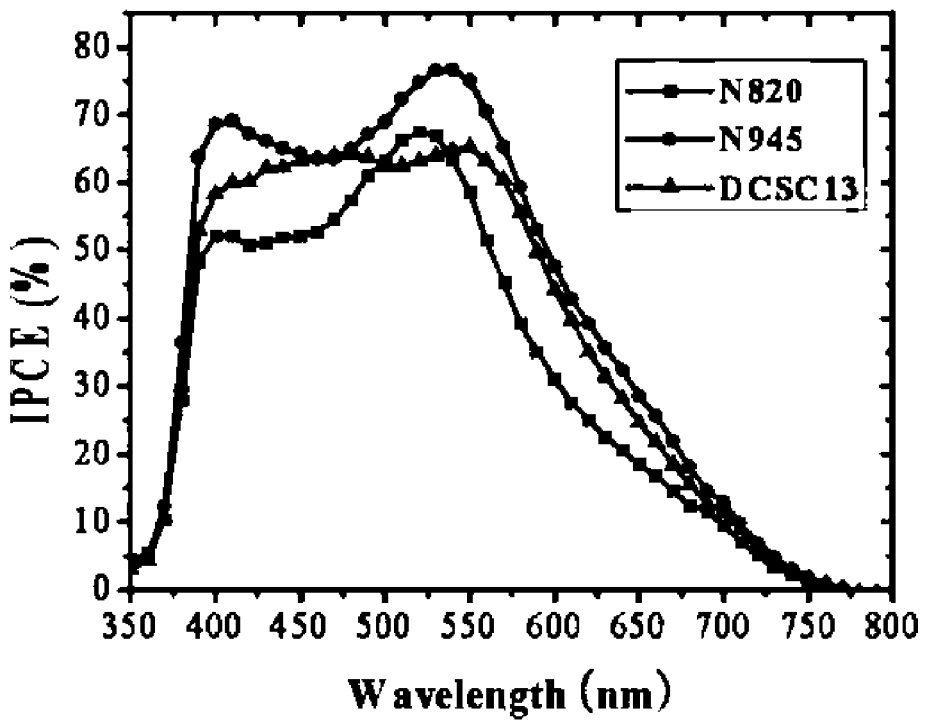

[Fig. 3]
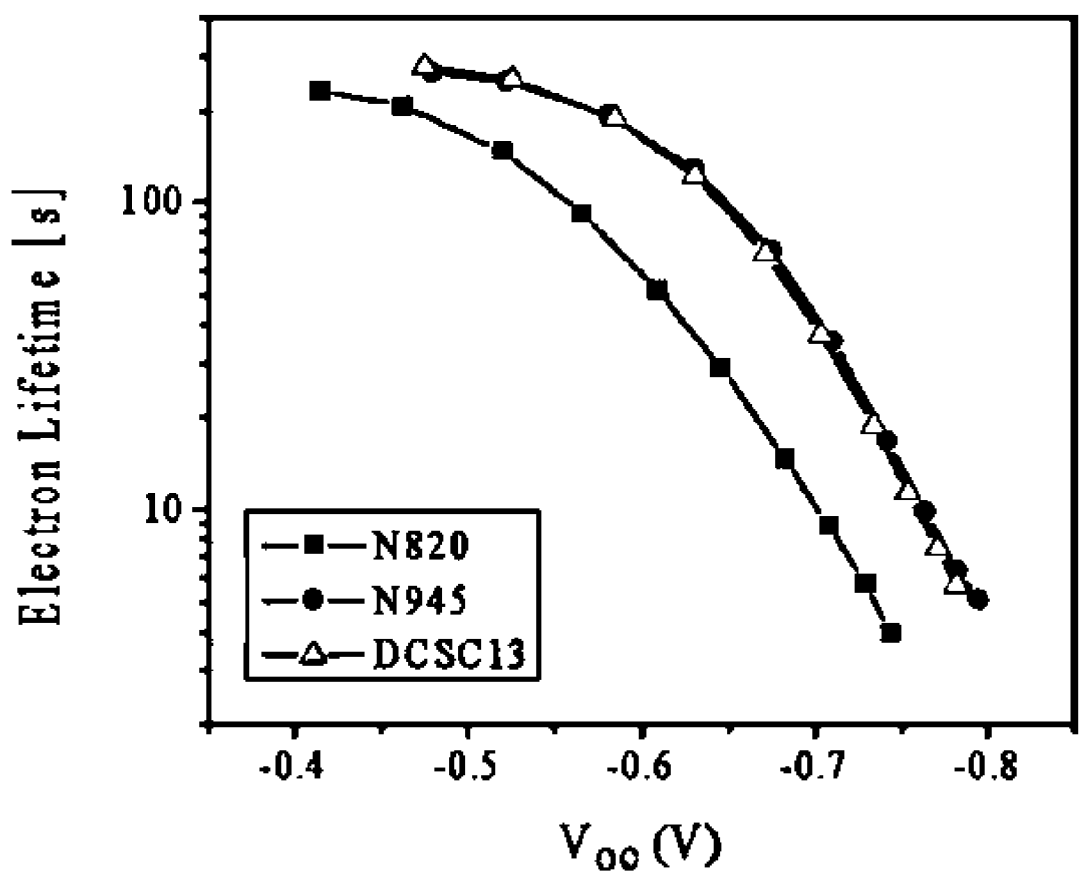

NOBLE RUTHENIUM-TYPE SENSITIZER AND METHOD OF PREPARING THE SAME

TECHNICAL FIELD

The present invention relates to a noble ruthenium-type sensitizer (dye) and a making method thereof, and more particularly, to a noble ruthenium-type dye (sensitizer) which is used to manufacture a dye-sensitized solar cell, drastically improves a molar extinction coefficient to enhance efficiency of a solar cell with only a small amount of a dye and oxide semiconductor particles, allows a thin film solar cell element to be manufactured without difficulty and sharply reduces manufacturing costs of a solar cell, a making method thereof and a photoelectric conversion element and a dye-sensitized solar cell including the same.

BACKGROUND ART

Since a research team of Michael Gratzel at the Ecole Polytechnique Federale de Lausanne (EPFL) in Switzerland developed a dye-sensitive nano particle titanium dioxide solar cell in 1991, lots of studies have been conducted on the area. The dye-sensitized solar cell requires significantly lower manufacturing costs than an existing silicon solar cell does, and can possibly replace an existing amorphous silicon solar cell. Unlike a silicon solar cell, the dye-sensitized solar cell is a photoelectrochemical solar cell which includes a dye molecule absorbing visible rays to generate an electron-hole pair and a transition metal oxide transferring a generated electron, as main materials.

Representative dyes which are used in a conventional dye-sensitized solar cell may include following compounds.

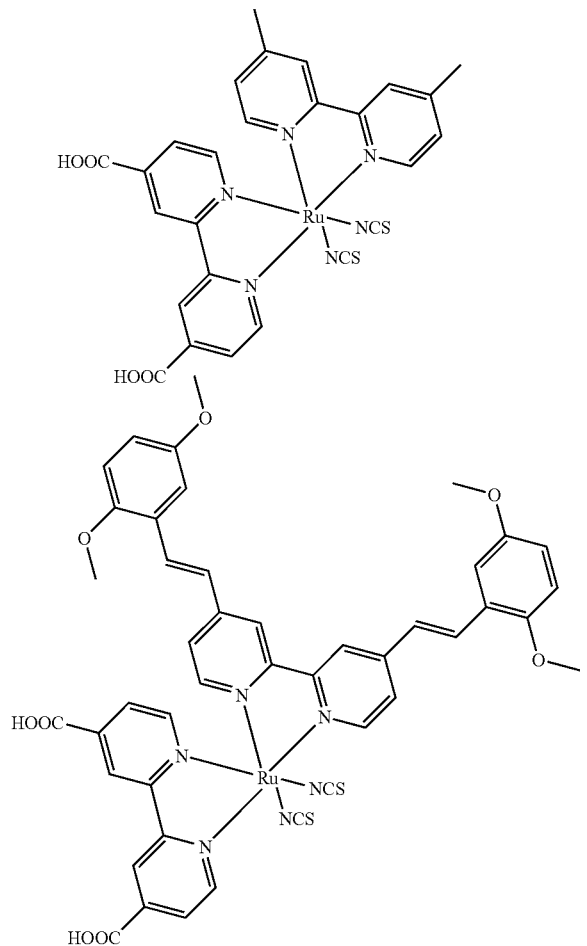

The foregoing conventional dyes are called N820 and N945, respectively.

If the conventional dyes are used to manufacture a solar cell, a 15 μm to 20 μm oxide semiconductor particle layer should be provided to apply the dyes thereto. However, the dye and the oxide semiconductor particles are very expensive and account for 30% or more manufacturing costs of the dye-sensitized solar cell. Thus, there have been consistent requests to develop a dye providing higher photoelectric conversion efficiency while the usage amount of the dyes and the oxide semiconductor particles is reduced. With the request for a thinner solar cell continued, studies on proper materials are being conducted.

DISCLOSURE OF INVENTION

Technical Problem

Accordingly, it is an aspect of the present invention to provide a dye which drastically improves molar extinction coefficient to enhance efficiency of a solar cell with only a small amount of a dye and oxide semiconductor particles, allows a thin film solar cell to be manufactured without difficulty and sharply reduces manufacturing costs of a solar cell, and a making method thereof.

Also, it is another aspect of the present invention to provide a manufacturing method of a dye-sensitized photoelectric conversion element which sharply reduces manufacturing costs by using a small amount of the dye and oxide semiconductor particles, and a manufacturing method of a solar cell including the same.

Additional aspects and/or advantages of the present invention will be set forth in part in the description which follows and, in part, will be obvious from the description, or may be learned by practice of the present invention.

Technical Solution

It provides ruthenium-type dye (sensitizer) which is represented by a following chemical formula 1, comprising

[Chemical formula 1]

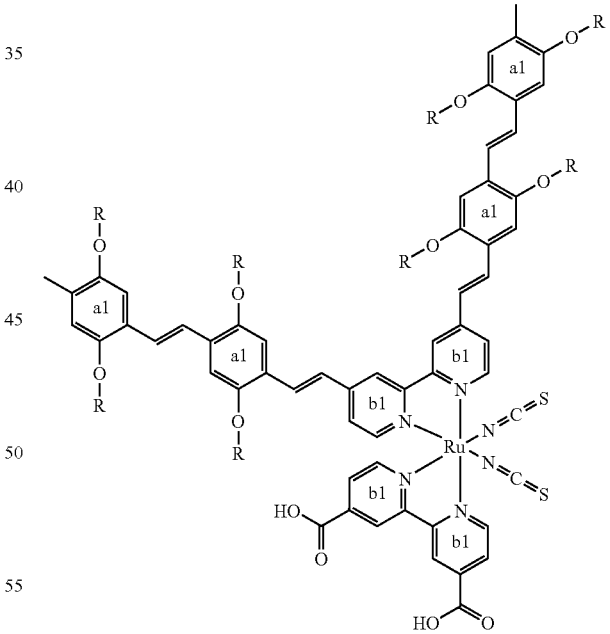

wherein, a ring a1 includes at least one substituent having a halogen atom, an amide group, a cyano group, a hydroxyl group, a nitro group, an alkoxyl group or an acyl group. A ring b1 includes at least one substituent having a halogen atom, an amide group, a cyano group, a hydroxyl group, a nitro group, an alkoxyl group or an acyl group. R is equal or different and includes a saturated or unsaturated alkyl group having 1 to 30 carbons, independently. R includes at least one substituent having a halogen atom, an amide group, a cyano group, a hydroxyl group, a nitro group, an alkoxyl group or an acyl group.

It also provides ruthenium-type dye (sensitizer) which is represented by a following chemical formula 2, comprising

[Chemical formula 2]

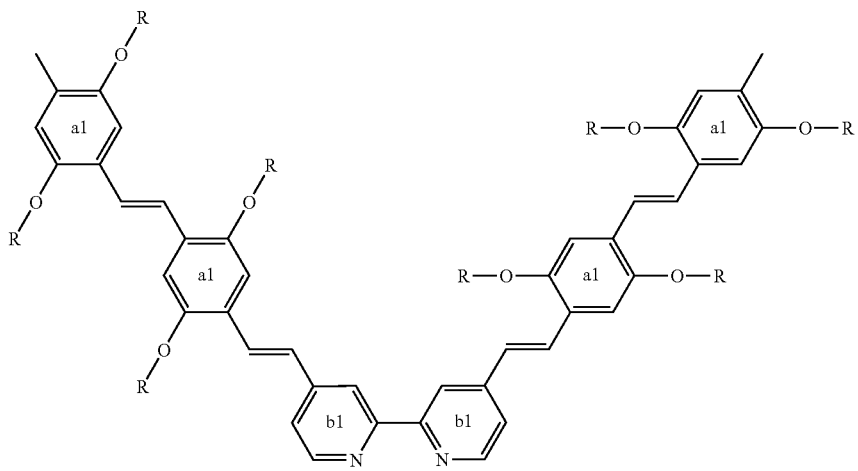

wherein, a ring a1 includes at least one substituent having a halogen atom, an amide group, a cyano group, a hydroxyl group, a nitro group, an alkoxyl group or an acyl group. A ring b1 includes at least one substituent having a halogen atom, an amide group, a cyano group, a hydroxyl group, a nitro group, an alkoxyl group or an acyl group. R is equal or different and includes a saturated or unsaturated alkyl group having 1 to 30 carbons, independently. R includes at least one substituent having a halogen atom, an amide group, a cyano group, a hydroxyl group, a nitro group, an alkoxyl group or an acyl group.

It also provides a making method of a dye represented by the chemical formula 1 in which a compound in a following chemical formula 4 reacts to compounds in chemical formulas 3, 5 and 6, the making method comprising

[RuCl$_2$(p-cymene)]$_2$     [Chemical formula 3]

[Chemical formula 4]

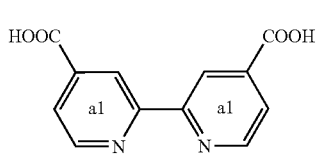

[Chemical formula 5]     NH$_4$NCS     [Chemical formula 6]

wherein, a1, b1 and R in the chemical formulas 3, 4, 5 and 6 are as defined above.

It also provides a making method of a dye represented by the chemical formula 2 in which a compound in a following chemical formula 7 reacts to compounds in chemical formulas 3, 4 and 6, the making method comprising

[RuCl$_2$(p-cymene)]$_2$     [Chemical formula 3]

[Chemical formula 4]

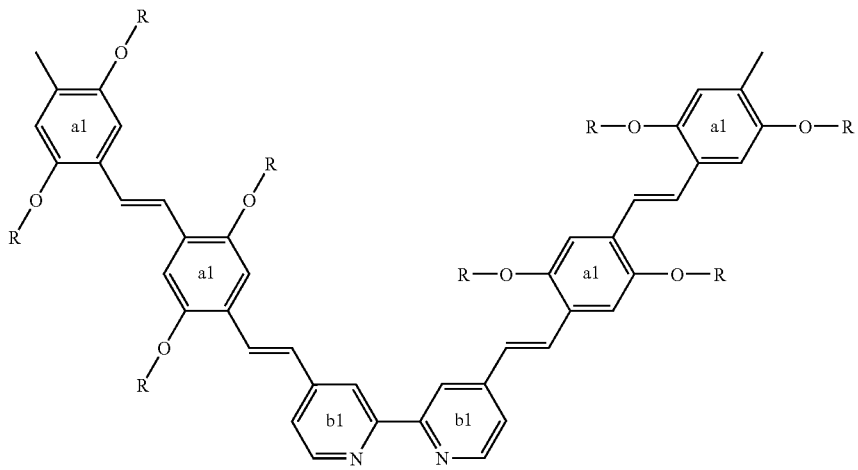

[Chemical formula 6]

NH₄NCS

[Chemical formula 7]

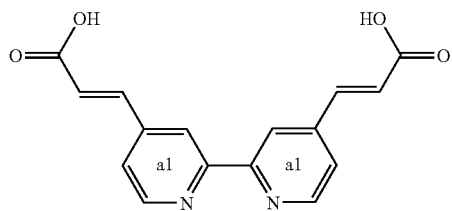

wherein, a1, b1 and R in the chemical formulas 3, 4, 6 and 7 are as defined above.

It also provides dye-sensitized photoelectric conversion element which comprises oxide semiconductor particles carrying the compound represented by the chemical formula 1 or 2 and a dye-sensitized solar cell which comprises the dye-sensitized photoelectric conversion element.

Advantageous Effects

As described above, the present invention provides a ruthenium-type dye which improves a molar extinction coefficient to enhance efficiency of a solar cell with only a small amount of a dye and oxide semiconductor particles, allows a thin film solar cell element to be manufactured without difficulty and sharply reduces manufacturing costs of a solar cell.

BRIEF DESCRIPTION OF THE DRAWINGS

The above and/or other aspects of the present invention will become apparent and more readily appreciated from the following description of the embodiments, taken in conjunction with the accompanying drawings of which:

FIG. 1 illustrates absorbance spectrum of solar cells which are manufactured with conventional dyes N820 and N945 and a dye DCSC13 according to an exemplary embodiment of the present invention;

FIG. 2 illustrates IPCE indices of the solar cells which are manufactured with the conventional dyes N820 and N945 and the dye DCSC13 according to the exemplary embodiment of the present invention; and FIG. 3 illustrates electron lifetime of the solar cells which are manufactured with the conventional dyes N820 and N945 and the dye DCSC13 according to the exemplary embodiment of the present invention.

MODE FOR THE INVENTION

Hereinafter, exemplary embodiments of the present invention will be described with reference to accompanying drawings, wherein like numerals refer to like elements and repetitive descriptions will be avoided as necessary.

Hereinafter, the present invention will be described in detail.

The present inventors have discovered that a dye according to the present invention provides improved molar extinction coefficient compared to a conventional dye, enhances efficiency of a solar cell by using a relatively small amount of the dye and oxide semiconductor particles, allows a thin film solar cell element to be manufactured without difficulty and sharply reduces manufacturing costs of a solar cell if a dye-sensitized solar cell is manufactured with oxide semiconductor particles carrying a compound represented by a chemical formula 1 or 2, and have completed the present invention.

A ruthenium-type dye (sensitizer) according to the present invention is represented by a following chemical formula 1 or 2.

[Chemical formula 1]

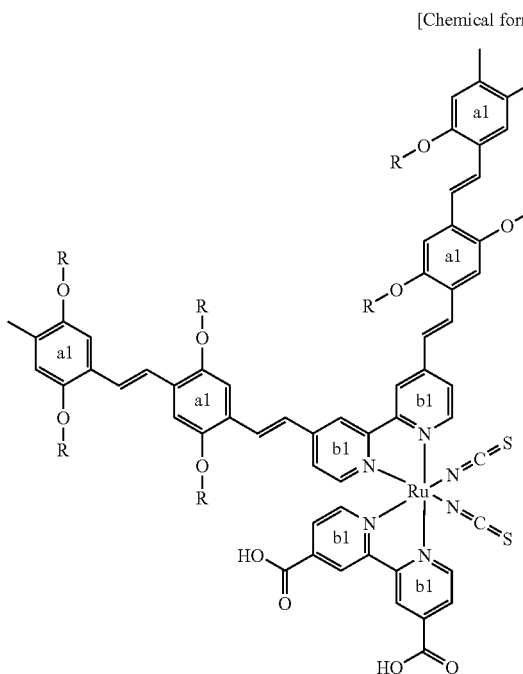

In the chemical formula 1, a ring a1 may include at least one substituent having a halogen atom, an amide group, a cyano group, a hydroxyl group, a nitro group, an alkoxyl group or an acyl group. A ring b1 may include at least one substituent having a halogen atom, an amide group, a cyano group, a hydroxyl group, a nitro group, an alkoxyl group or an acyl group. R may be equal or different and include a saturated or unsaturated alkyl group having 1 to 30 carbons, independently. R may include at least one substituent having a halogen atom, an amide group, a cyano group, a hydroxyl group, a nitro group, an alkoxyl group or an acyl group.

[Chemical formula 2]

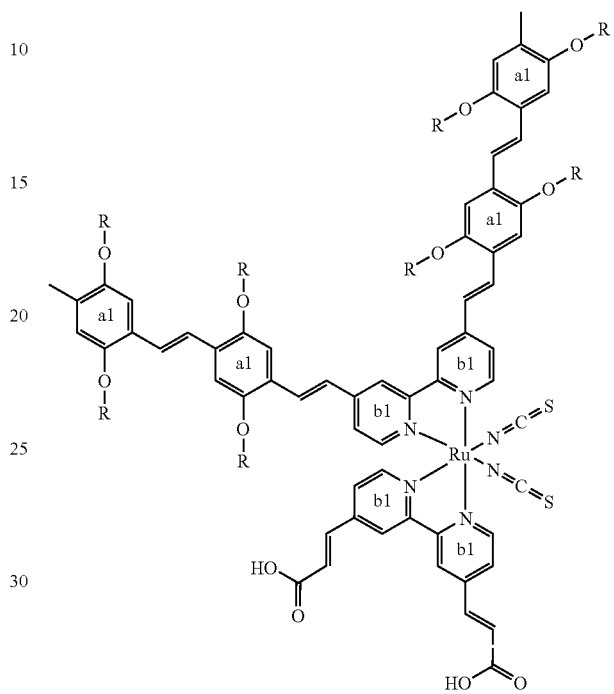

In the chemical formula 2, a ring a1 may include at least one substituent having a halogen atom, an amide group, a cyano group, a hydroxyl group, a nitro group, an alkoxyl group or an acyl group. A ring b1 may include at least one substituent having a halogen atom, an amide group, a cyano group, a hydroxyl group, a nitro group, an alkoxyl group or an acyl group. R may be equal or different and include a saturated or unsaturated alkyl group having 1 to 30 carbons, independently. R may include at least one substituent having a halogen atom, an amide group, a cyano group, a hydroxyl group, a nitro group, an alkoxyl group or an acyl group.

R in the compound represented by the chemical formula 1 or 2 preferably includes an alkyl compound having 1 to 5 carbons, and more preferably includes one of following compounds.

DCSC 13

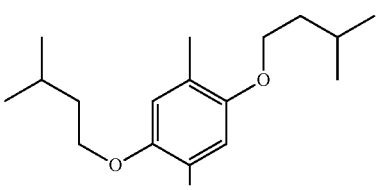

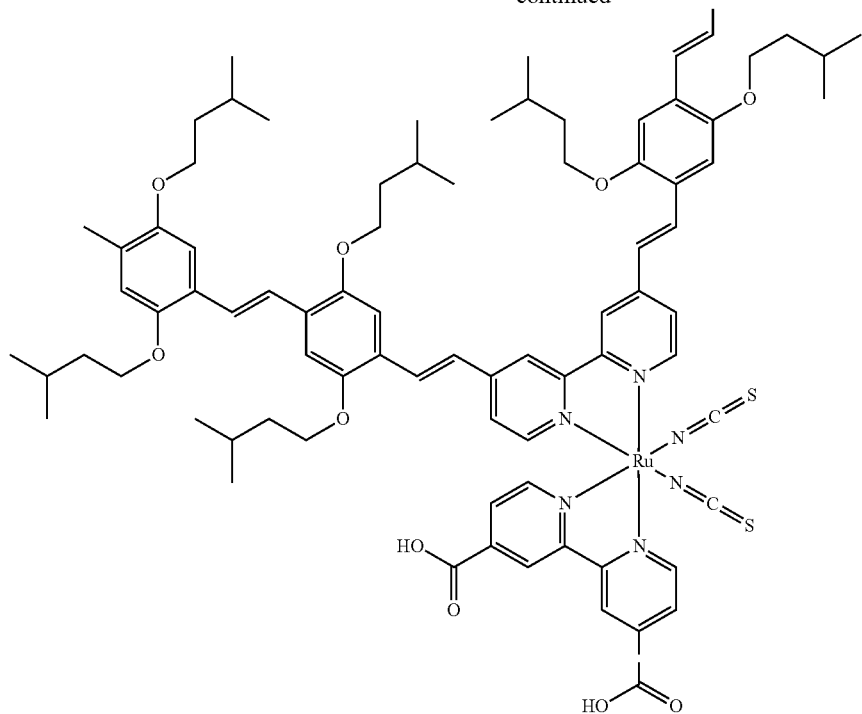
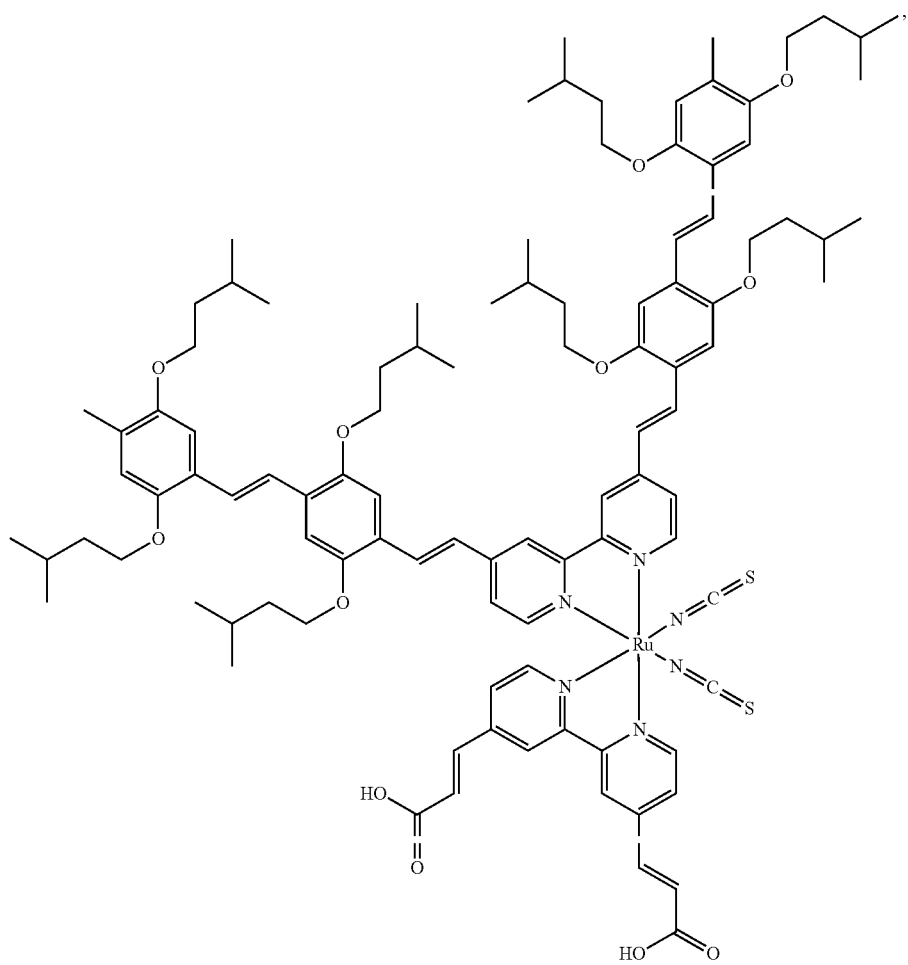
DCSC 14

-continued

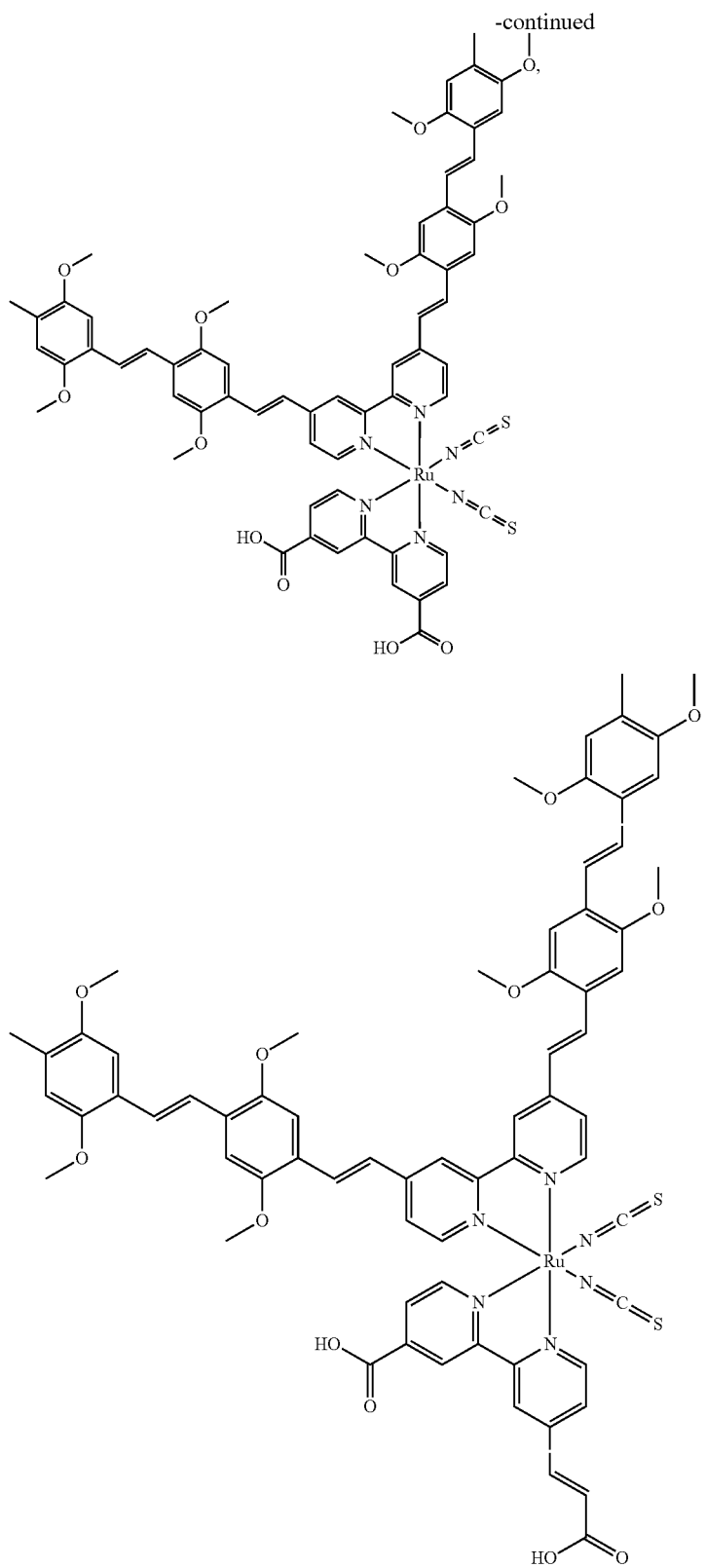

Also, the present invention provides a making method of the dye which is represented by the chemical formula 1 or 2. The dye which is represented by the chemical formula 1 or 2 may be made by double Wadwordth-Emmons reaction between i) a compound in Chemical formula 4 and ii) a compound in Chemical formula 3, iii) a compound in Chemical formula 5 or 7 or iv) a compound in Chemical formula 6.

[RuCl$_2$(p-cymene)]$_2$  [Chemical formula 3]

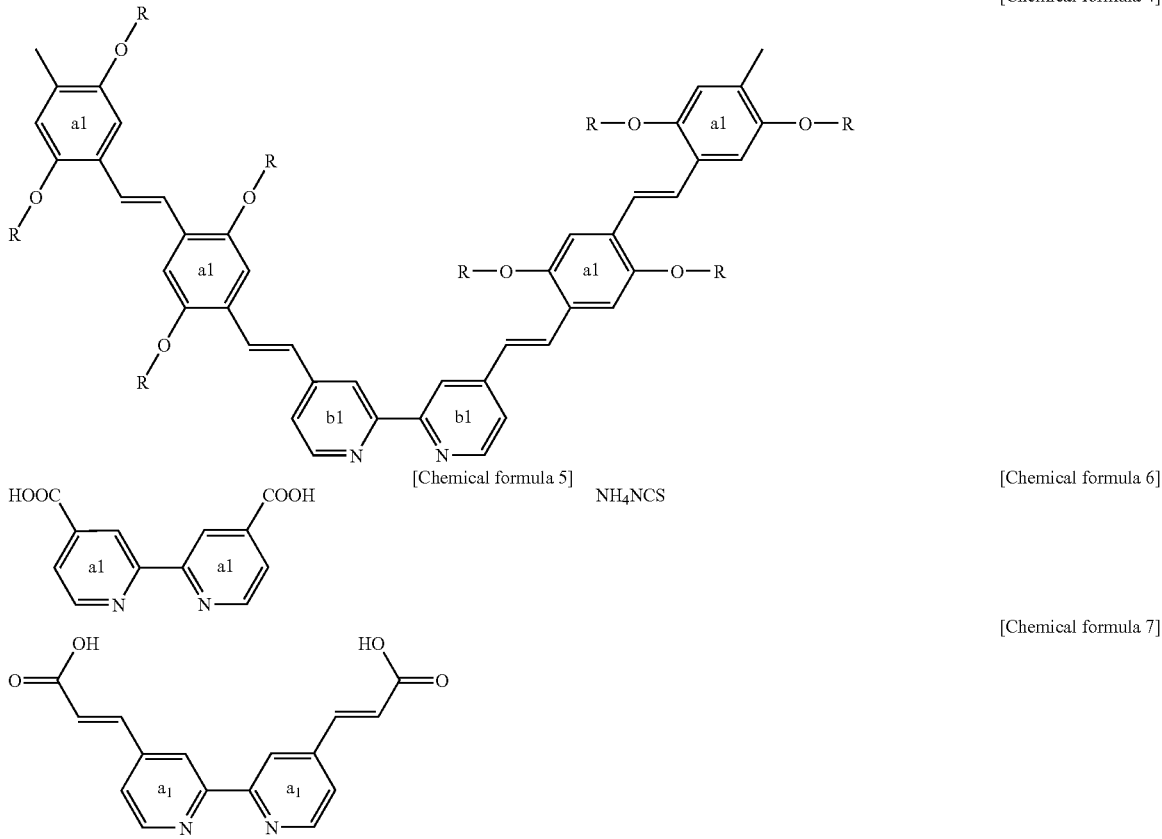

a1, b1 and R in the chemical formulas 3, 4, 5, 6 and 7 are as defined above.

Further, the present invention provides a dye-sensitized photoelectric conversion element. The dye-sensitized photoelectric conversion element includes oxide semiconductor particles carrying the dye represented by the chemical formula 1 or 2. The dye-sensitized photoelectric conversion element according to the present invention may be manufactured with conventional dyes to be included in a solar cell, as well as manufactured with the dye represented by the chemical formula 1 or 2. Preferably, the dye-sensitized photoelectric conversion element according to the present invention is manufactured by forming an oxide semiconductor layer on a substrate with the oxide semiconductor particles and then by applying the dye according to the present invention to the thin film.

The substrate which has the oxide semiconductor particles layer according to the present invention preferably has a conductive surface. A commercially available substrate may be used. More specifically, the substrate may include a glass or a transparent high molecular material such as polyethylenephthalate or polyethersulfone on which a conductive metal oxide layer such as tin oxide including indium, fluorine and antinomy or a metal layer such as steel, silver, gold and the like is formed. The conductivity is preferably 1000Ω and below, and more preferably 100Ω and below.

The particles of oxide semiconductor preferably include metal oxide. More specifically, the metal oxide may include titan, tin, zinc, tungsten, zirconium, gallium, indium, yttrium, niobium, tantalum, vanadium and the like. The metal oxide preferably includes titan, tin, zinc, niobium, indium and the like, and more preferably titanium dioxide, zinc oxide and tin oxide and most preferably titanium dioxide. The oxide semiconductor may be solely used, mixed with others or coated on a surface of a semiconductor.

A diameter of the oxide semiconductor particles is an average of 1 to 500 nm, and more preferably 1 to 100 nm. The oxide semiconductor particles may include large and small diameters combined. Alternatively, the oxide semiconductor particles may include multiple layers.

The oxide semiconductor layer may be formed by spraying oxide semiconductor particles on a substrate, by electrically extracting a semiconductor particles layer from a substrate as an electrode or by applying a paste on a substrate to be dried, cured or fired. The paste includes particles which are created by hydrolyzing a precursor of semiconductor particles such as slurry of semiconductor particles or semiconductor alkoxide and the like. Preferably, the oxide semiconductor layer is formed by applying the paste on the substrate. In this case, the secondary-coagulated oxide semiconductor particles are dispersed in a dispersion medium by a known method to have an average primary diameter of 1 to 200 nm to thereby form the slurry.

The dispersion medium which disperses the slurry may vary as long as it disperses the semiconductor particles. More specifically, the dispersion medium may include water, alcohol such as ethanol, ketone such as acetone, acetyl acetone or hydrocarbon such as hexane, which may be mixed to be used. Preferably, the dispersion medium includes water since it less changes viscosity of the slurry. A dispersion stabilizer may be used to stabilize dispersion of the oxide semiconductor particles. More specifically, the dispersion stabilizer may include e.g., acid such as acetic acid, hydrochloric acid and nitric acid, acetyl acetone, acrylic acid, polyethyleneglycol, polyvinylalcohol and the like.

The substrate which is applied with the slurry may be fired at firing temperatures of 100° C. and above, and preferably 200° C. and above. The upper limit of the firing temperatures is the melting point (softening point) of the material, i.e., 900° C., and preferably 600° C. and below. The firing temperatures according to the present invention are not limited particularly, but preferably within 4 hours.

According to the present invention, a thickness of the layer on the substrate may be 1 to 200 μm, and preferably 1 to 50 μm. If the substrate is fired, some of the oxide semiconductor particles layer are melted and attached, but do not affect the present invention particularly.

The oxide semiconductor layer may be secondary treated. For example, the layer may be applied with a solution of alkoxide, chloride, nitride and sulfide which are the same metal as a semiconductor, and then dried or fired again to improve performance. The metal alkoxide may include titanethoxide, titaniumisoproepoxide, titan t-butoxide, n-dibutyldiacetyl tin and the like, or an alcohol solution thereof. The chloride may include e.g., titanium tetrachloride, tin tetrachloride, zinc chloride and the like, or an aqueous solution thereof. The obtained oxide semiconductor layer includes particles of the oxide semiconductor.

A method of applying the dye to the oxide semiconductor particles layer according to the present invention is not limited to a particular method. More specifically, the substrate having the oxide semiconductor layer may be dipped into a solution which is made by dissolving the dye represented by the chemical formula 1 or 2 with a solvent or dipped into a dispersion solution which is made by dispersing the dye. The concentration of the solution or the dispersion solution may be properly determined depending on the dye. The applying temperature ranges from normal temperatures to the boiling point of the solvent. The applying time ranges from one minute to 48 hours. More specifically, the solvent which dissolves the dye may include e.g., methanol, ethanol, acetonitrile, dimethylsulfoxide, dimethylformamide, acetone, t-butanol, etc. The dye concentration of the solution is typically $1 \times 10^{-6}$ M to 1 M, and preferably $1 \times 10^{-5}$ M to $1 \times 10^{-1}$ M. Thus, the present invention may provide a dye-sensitized photoelectric conversion element which includes the oxide semiconductor particles layer.

The dye which is represented by the chemical formula 1 or 2 according to the present invention may include a single or several dyes mixed. If the dyes are mixed, only the dyes according to the present invention may be used, or other dyes or metal complex dyes may be mixed together. The metal complex dye to be mixed may include e.g., ruthenium complex or triarylmethylium salt thereof written in M. K. Nazeeruddin, A. Kay, I Rodicio, R Humphry-Baker, E Muller, P. Liska, N. Vlachopoulos and M Gratzel, J. Am. Chem. Soc., 1993, vol. 115, p. 6382, phthalocyanine, porphyrin, etc. The organic dye to be mixed may include metal-free phthalocyanine, porphyrine, cyanine, merocyanine, oxonol, triphenylmethane, metin dye such as acrylic acid dye disclosed in WO2002/011213, xanthen dye, azo dye, anthraquinone dye, perylene dye and the like. If two or more dyes are used, the dyes may sequentially be applied to the semiconductor layer or may be mixed together to be applied to the semiconductor layer.

If the oxide semiconductor particles layer according to the present invention is dipped into the dyes, the layer may be dipped into the dye under the presence of an inclusion compound to prevent the dyes from being bonded to one another.

The inclusion compound may include cholic acid such as deoxycholic acid, dehydrodeoxycholic acid, chenodeoxycholic acid, cholic acid methylester, cholic acid natrium and the like, a steroid compound such as polyethyleneoxide, cholic acid and the like, crown ether, cyclodextrin, calixarene, polyethyleneoxide, etc.

After being dipped into the dye, the electrode surface of the semiconductor layer may be treated by an amine compound such as 4-t-butyl pyridine or by a compound such as acetic acid, propionic acid which has an acidic group. For example, the substrate which has the semiconductor particles layer carrying the dye may be dipped into an ethanol solution of amine.

Further, the present invention provides a dye-sensitized solar cell which includes the dye-sensitized photoelectric conversion element. The solar cell may be manufactured by a known method by using a conventional photoelectric conversion element as well as using the dye-sensitized photoelectric conversion element having the oxide semiconductor particles layer carrying the dye represented by the chemical formula 1 or 2. More specifically, the dye-sensitized solar cell may include an electrode (negative) of a photoelectric conversion element which is formed by applying the dye represented by the chemical formula 1 or 2 to the oxide semiconductor particles layer, a counter electrode (positive), a redox electrolyte, a hole transferring material or a p-type semiconductor.

Preferably, the manufacturing method of the dye-sensitized solar cell according to the present invention includes an operation of coating $TiO_2$ paste on a transparent conductive substrate, an operation of firing the paste-coated substrate to form a $TiO_2$ layer, an operation of dipping the substrate having the $TiO_2$ layer to a solution including the dissolved dye represented by the chemical formula 1 or 2 to form a $TiO_2$ film electrode having the dye, an operation of providing a second glass substrate including a counter electrode on the $TiO_2$ film electrode, an operation of forming a hole to pass through the second glass substrate and the counter electrode, an operation of coupling the counter electrode and the $TiO_2$ film electrode by heat and pressure, leaving a thermoplastic polymer film therebetween, an operation of injecting an electrolyte to the thermoplastic polymer film interposed between the counter electrode and the $TiO_2$ film electrode through the hole and an operation of sealing the thermoplastic polymer film.

The redox electrolyte, the hole transferring material and the p-type semiconductor may be liquid, coagulate (gel and gel phase), solid, etc. The redox electrolyte, the hole transferring material and the p-type semiconductor may be liquid by being dissolved by a solvent or may include normal temperature-molten salt. The redox electrolyte, the hole transferring material and the p-type semiconductor may be coagulate (gel and gel phase) by being included in a polymer matrix or a monomer gelation agent. The redox electrolyte, the hole transferring material and the p-type semiconductor may be solid themselves.

The hole transferring material may include an amine derivative, a conductive polymer such as polyacetylene, polyaniline, polythiophene, a material such as a triphenylene compound using a discotheque liquid crystal phase, etc. The p-type semiconductor may include CuI, CuSCN and the like. Preferably, the counter electrode is conductive and acts as a catalyst for a reduction reaction of the redox electrolyte. For example, platinum, carbon, rhodium, ruthenium may be deposited on a glass or a polymer film, or conductive particles may be applied to the glass or the polymer film to form the counter electrode.

The redox electrolyte of the solar cell according to the present invention may include a halogen oxidation reduction electrolyte including a halogen compound having a halogen ion as a counter ion and a halogen molecule, a metal oxidation reduction electrolyte such as ferrocyanide-ferrocyanide, ferrocene-ferrocinium ion or a metal complex such as a cobalt complex, an organic oxidation reduction electrolyte such as alkylthiol-alkyldisulfide, viologen dye and hydroquinone-quinone and the like. Preferably, the redox electrolyte includes a halogen oxidation reduction electrolyte. Preferably, the halogen molecule of the halogen oxidation reduction electrolyte including the halogen compound-halogen molecule includes an iodine molecule. The halogen compound which has a halogen ion as a counter ion may include halogenated metal salt such as LiI, NaI, KI, $CaI_2$, $MgI_2$, CuI, halogen organic ammonium salt such as tetraalkylammoniumiodine, imidazoliumiodine, phyridiumiodine, or $I_2$.

The redox electrolyte may include a solution added with the foregoing materials. In this case, a solvent may electrochemically be inactive. More specifically, the solvent may include e.g., acetonitrile, propylenecarbonate, ethylenecarbonate, 3-methoxypropionitrile, methoxyacetonitrile, ethyleneglycol, propyleneglycol, diethyleneglycol, triethyleneglycol, butylolactone, dimethoxyethane, dimethylcarbonate, 1,3-dioxolane, methylformate, 2-methyltetrahydrofuran, 3-methoxy-oxazolidine-2-on, sulforane, tetrahydrofurane, water and the like. Preferably, the solvent includes acetonitrile, propylenecarbonate, ethylenecarbonate, 3-methoxypropionitrile, ethyleneglycol, 3-methoxy-oxazolidine-2-on, butylolactone, etc. The solvent may be solely used or mixed together to be used. The gel phase positive electrolyte may be formed by adding an electrolyte or an electrolyte solution to a matrix such as oligomer and polymer or by adding an electrolyte or an electrolyte solution to a monomer gelation agent. The concentration of the redox electrolyte may be 0.01 to 99 wt %, and more preferably 0.1 to 30 wt %.

The solar cell according to the present invention may be manufactured by providing the photoelectric conversion element (negative) having the oxide semiconductor particles carrying the dye and the counter electrode (positive) facing the photoelectric conversion element and by injecting the solution including the redox electrolyte therebetween.

The photoelectric conversion element and the solar cell according to the present invention include a novel dye having a drastically enhanced molar extinction coefficient. Thus, efficiency of the solar cell is great with only a small amount of dye and oxide semiconductor particles. Also, the thin film solar cell element is manufactured without difficulty and manufacturing costs of the solar cell are sharply reduced.

Hereinafter, exemplary embodiments of the present invention are provided to help understand the present invention. However, the present invention is not limited to following exemplary embodiments.

[Exemplary Embodiments]

[Exemplary Embodiment 1] Synthesis of Dye

The ruthenium-type dye (sensitizer) according to the present invention was synthesized through following reactions.

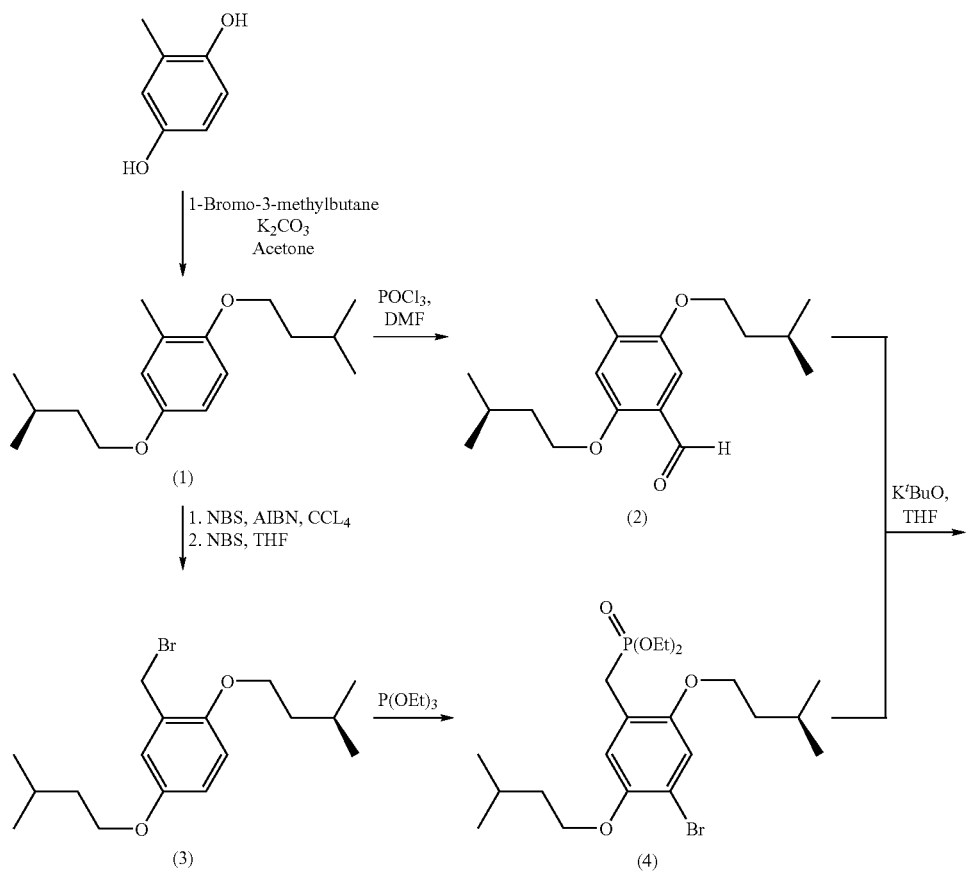

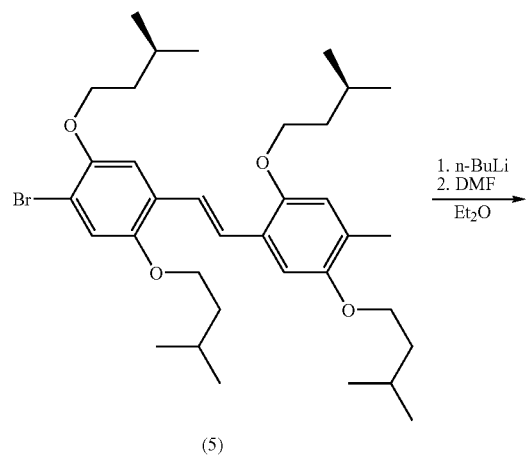
(5)
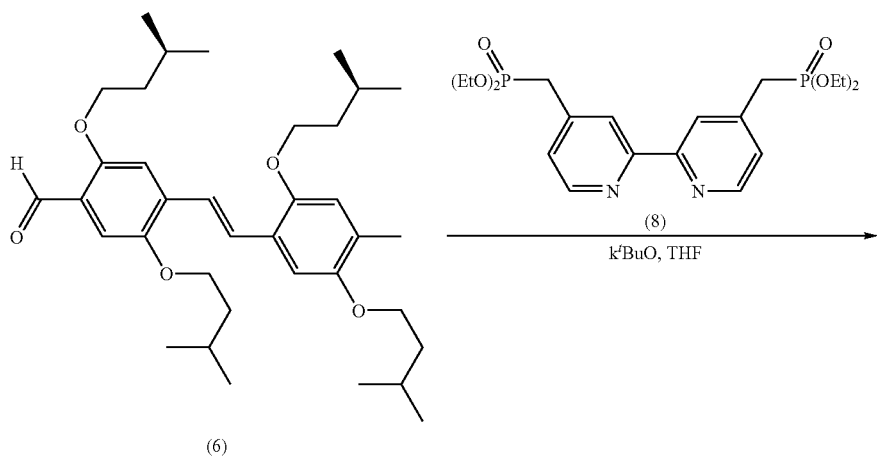
(6)
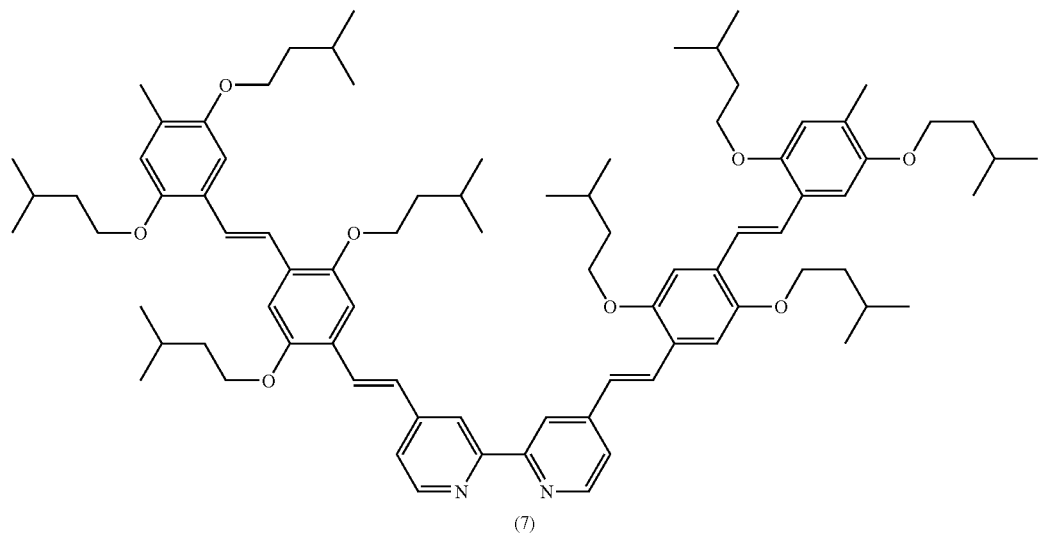
(7)

All reactions were implemented under argon condition, and all THF and diethylether solvent used were distilled. 1H, 13C NMR and 31P NMR used include Varian Mercury 300 spectrometer, and an absorbance spectrophotometer used includes Perkin-Elmer Lambda 2S UV-visible spectrophotometer. All starting materials include reagents of Aldrich and Strem without purification. An intermediate material includes 4,4'-diformyl-2,2'-bipyridine and 4,4'-bis(carboxyvinyl)-2,2'-bipyridine which were referred to from Tetrahedron Letters Journal, 1996, vol. 37, p. 7503 and Inorganic Chemistry Journal, 2005, vol. 44, p. 178.

a. 1,4-bis[3-methylbutoxy]-2-methylbenzene (1)

Under argon condition, methylhydroquinone (10.0 g, 81 mmol) and $K_2CO_3$ (5567 g, 403 mmol) were melted with 20 mL acetone and then added with 1-bromo-3-methylbutane (26.77 g, 177 mmol). Then, the mixture was agitated at reflux temperatures for 24 hours and then the temperature of the mixture was lowered to normal temperatures. After removing the solvent therefrom, the mixture was purified by column chromatography. (silica gel, $CH_2Cl_2$/hexane 1:4, Rf: 0.5). transparent oil. 1H NMR ($CDCl_3$): 6.77 (d, 1H), 6.75 (s, 1H), 6.70 (d, 1H), 3.95 (m, 4H), 2.23 (s, 3H), 1.86 (m, 2H), 1.69 (m, 4H), 0.99 (m, 12H); 13C {1H} NMR ($CDCl_3$): 152.9, 151.6, 128.2, 117.8, 112.2, 111.7, 67.2, 67.0, 38.4, 38.3, 25.3, 25.2, 22.8, 22.7, 16.5. Anal. Calcd, for $C_{17}H_{28}O_2$: C, 77.22; H, 10.67. Found: C, 77.05; H, 10.58.

b. 2,5-bis[3-methylbutoxy]-4-methylbenzaldehyde (2)

Under argon condition, $POCl_3$ (13.92 g, 90.77 mmol) was added to a No. 1 compound (6 g, 2269 mmol) and a DMF compound (6.6 g, 90.77 mmol) to be refluxed for 12 hours. The temperature of the reaction solution was lowered to normal temperatures, and then ice water of 100 mL was slowly added thereto. The reaction solution was agitated for one hour and then extracted by diethylether of 200 mL. An organic layer was cleansed three times with 100 mL 1 M HCl solution and then another three times with 100 mL water by using a separatory funnel. The organic layer was dried and then purified by column chromatography. (silica gel, $CH_2Cl_2$/hexane 1:2, Rf: 0.4). crystalloid transparent solid. 1H NMR ($CDCl_3$): 10.40 (s, 1H), 7.22 (s, 1H), 6.79 (s, 1H), 4.04 (t, 2H), 3.97 (t, 2H), 2.26 (s, 3H), 1.83 (m, 2H), 1.69 (m, 4H), 0.96 (m, 12H); 13C{1H} NMR ($CDCl_3$): 189.5, 156.3, 151.5, 136.9, 123.1, 115.7, 108.3, 67.6, 66.9, 38.1, 38.0, 25.3, 25.2, 22.8, 22.7, 17.4. Anal. Calcd. for $C_{18}H_{28}O_3$: C, 73.93; H, 9.65 Found: C, 73.74; H, 9.57.

c. 1-bromo-2,5-bis[3-methylbutoxy]-4-bromomethylbenzene (3)

Under argon condition, after melting the No. 1 compound (5.0 g, 18.9 mmol) with 30 mL $CCl_4$, NBS (4.0 g, 227 mmol) and AIBN (1.1 g, 6.8 mmol) were added to the No. 1 compound to be agitated at reflux temperatures for one hour. The temperature of the reaction solution was lowered to normal temperatures and then the solution was filtered by filter paper. The filtered solution was dried, received 60 ml hexane and then filtered again. The filtered solution was dried again, and then melted by 30 mL THL. NBS (4.4 g, 24.6 mmol) was added to the solution to be agitated at reflux temperatures for one hour. The temperature of the mixture was lowered to normal temperatures, and the filtered solution was dried again. After adding 60 mL hexane, the solution was filtered again. The filtered solution was dried again, recrystallized with ethanol and then purified. White powdered solid. 1H NMR ($CDCl_3$): 7.06 (s, 1H), 6.90 (s, 1H), 4.50 (s, 2H), 3.99 (t, 4H), 1.89 (m, 2H), 1.71 (m, 4H), 0.99 (m, 6H), 0.96 (t, 6H), 13C{1H}NMR ($CDCl_3$): 151.7, 150.0, 126.6, 117.9, 116.5, 113.7, 69.1, 68.1, 38.7, 38.5, 29.0, 25.7, 25.6, 23.2, 23.1, Anal. Calcd. for $C_{17}H_{26}Br_2O_2$: C, 48.36; H, 6.21. Found: C, 48.11; H, 6.11.

d. diethyl{2,5-bis[3-methylbutoxy]-4-bromo-benzyl}-phosphite (4)

The excessive amount of triethyl phosphite, 10 mL, and a No. 3 compound (3.2 g, 7.6 mmol) were agitated at 160° C. for 1.5 hours, and the excessive amount of triethyl-phosphite was removed in a vacuum. White solid. 1H NMR ($CDCl_3$): 7.03 (s, 1H), 6.96 (d, JH-P=2.7 Hz, 1H), 4.02 (q, 4H), 3.92 (t, 4H), 3.17 (d, 2H, JH-P=21.9 Hz), 1.84 (m, 2H), 1.67 (m, 4H), 1.24 (t, 6H), 0.96 (d, 6H), 0.94 (d, 6H); 13C {1H} NMR ($CDCl_3$): 151.9, 149.3, 127.1, 117.0, 116.4, 109.0, 76.2, 68.9, 67.4, 38.3, 38.2, 25.3, 25.2, 22.8, 22.7, 22.2, 16.4; 31P NMR ($CDCl_3$): 20.95 Anal. Calcd. for $C_{21}H_{36}BrO_5P$: C, 52.61; H, 7.57. Found: C, 52.46; H, 7.48.

e. 4-{4-methyl-2,5-bis[3-methylbutoxy]styryl}-2,5-bis[3-methylbutoxy]bromo benzene (5)

Under argon condition, 30 mL THF was added to a No. 4 compound (250 g, 5.2 mmol) and t-BuOK (0.70 g, 6.2 mmol) to be melted. The solution was slowly mixed with another solution formed by melting a No. 2 compound (1.52 g, 5.2 mmol) with 20 mL THF. The mixture was agitated at normal temperatures for 8 hours. Then, small, broken ice of 60 g and 5 M hydrochloric acid of 20 mL were added to the mixture. Then, 30 mL chloroform solution was extracted from the mixture three times. The extracted organic solvent was dried and recrystallized with ethanol. Yellow solid powder. 1H NMR ($CDCl_3$): 7.44 (d, 1H), 7.32 (d, 1H), 7.16 (s, 1H), 7.07 (s, 1H), 7.06 (s, 1H), 6.73 (s, 1H), 4.00 (m, 8H), 2.23 (s, 3H), 1.89 (m, 4H), 1.73 (m, 8H), 0.99 (m, 12H), 0.97 (m, 12H), 13C{1H}NMR ($CDCl_3$): 151.6, 150.9, 150.5, 149.9, 127.9, 127.5, 124.8, 124.2, 121.7, 117.8, 116.0, 111.6, 111.2, 109.0, 68.6, 68.3, 68.0, 67.1, 38.5, 38.4, 38.2, 38.1, 25.5, 25.4, 25.3, 25.1, 22.9, 22.8, 22.7, 22.6, 16.6. Anal. Calcd. for $C_{35}H_{53}BrO_4$: C, 68.06; H, 8.65 Found: C, 68.04; H, 8.58.

f. 4-{4-methyl-2,5-bis[3-methylbutoxy]styryl}-2,5-bis[3-methylbutoxy]benzaldehyde (6)

After melting a No. 5 compound (1.7 g, 275 mmol) with 30 mL diethylether, 1.6 M n-butyllithium (21 mL, 3.3 mmol) which was melted in hexane at −10° C. was slowly added to the solution. The mixture was agitated at −10° C. for 30 minutes, received DMF (0.97 mL, 1256 mmol) at normal temperatures to be agitated at normal temperatures for 3 hours. After the reaction, 6 M HCl (20 mL) was added to the mixture. Then, an organic layer was separated from the mixture by using a separatory funnel and then cleansed with 100 mL water. The solvent of the organic layer was dried and purified by column chromatography. ($CH_2Cl_2$/hexane 1:1, Rf: 0.4). yellow solid powder. 1H NMR ($CDCl_3$): 10.43 (s, 1H), 7.60 (d, 1H), 7.44 (d, 1H), 7.32 (s, 1H), 7.22 (s, 1H), 7.08 (s, 1H), 6.74 (s, 1H), 4.04 (m, 8H), 2.24 (s, 3H), 1.88 (m, 4H), 1.75 (m, 8H), 1.00 (m, 12H), 0.98 (m, 12H) 13C{1H} NMR ($CDCl_3$): 189.3, 156.4, 151.7, 150.9, 150.6, 135.5, 128.9, 127.3, 124.3, 123.9, 121.5, 116.0, 110.1, 110.0, 109.2, 68.0, 67.6, 67.4, 67.2, 38.4, 38.3, 38.2, 38.1, 25.5, 25.4, 25.3, 25.2, 22.9, 22.8, 22.7, 22.6, 16.7. Anal. Calcd. for $C_{36}H_{54}O_5$: C, 76.28H, 9.60. Found: C, 76.02H, 9.59.

g. OPV Ligand (7)

A No. 8 compound (0.24 g, 0.5 mmol) which had been synthesized by a synthesis method written in Inorganic Chemistry, 1991, vol. 30, p. 2942, was melted by 20 mL THF under argon condition. Then, a No. 6 compound (0.66 g, 1.2 mmol) which had been melted with 20 mL THF was slowly added to the solution to be agitated at normal temperatures for 8 hours. After being reacted in a vacuum, the solvent was removed from the mixture. 5 M hydrochloric acid solution of 20 mL was added to the mixture. The mixture was extracted three times by 20 mL with dichloro methane. The solvent was dried again, and remaining materials were purified by column chromatography. (ethyl acetate/hexane 1:3, Rf: 0.4) Yellow solid powder. 1H NMR (CDCl$_3$): 8.67 (s, 2H, J=5.1 Hz, pyridine), 8.52 (s, 2H, pyridine), 7.79 (d, 2H, J=16.5 Hz, vinyl-H), 7.51 (d, 2H, J=16.2 Hz, vinyl-H), 7.44 (d, 2H, J=5.7 Hz, pyridine), 7.43 (d, 2H, J=16.2 Hz, vinyl-H), 7.21 (d, 2H, J=16.5 Hz, vinyl-H), 7.20 (s, 2H), 7.15 (s, 2H), 7.10 (s, 2H), 6.74 (s, 2H), 4.10 (m, 8H), 4.06 (m, 8H), 2.24 (s, 6H), 1.92 (m, 8H), 1.79 (m, 16H), 1.01 (m, 48H) 13C{1H} NMR (CDCl$_3$): 156.7, 151.7, 151.6, 150.8, 150.6, 149.5, 146.6, 129.1, 128.4, 128.0, 126.2, 125.1, 125.0, 124.3, 121.9, 120.5, 119.0, 116.1, 111.1, 110.0, 109.0, 68.1, 68.0, 67.8, 67.2, 38.5, 38.4, 38.3, 38.2, 25.6, 25.5, 25.4, 25.3, 22.9, 22.8, 16.6. Anal. Calcd. for C$_{36}$H$_{54}$O$_5$: C, 78.71H, 9.12. Found: C, 78.58H, 9.05.

h. [Ru(II)LL'(NCS)$_2$] (L=OPV ligand, L'=4,4'-bis(carboxylic acid)-2,2'-bipyridine), DCSC-13

A No. 7 compound (0.22 g, 0.17 mmol) as OPV ligand and dichloro(p-cymene)ruthenium(II) dimmer (0.051 g, 0.084 mmol) were added with a DMF solvent and agitated at 80° C. for 4 hours. 4,4'-dicarboxylic acid-2,2'-bipyridine (41 mg, 0.17 mmol) was added to the mixture and agitated at 160° C. for another 4 hours. Then, ammonium thiocyanate (0.19 g, 2.7 mmol) was added to the mixture and agitated at 130° C. for 4 hours, and the solvent was removed in a vacuum. Water of 200 mL was added to form sediment and then the mixture was filtered. The filtered solid was dried and then melted by 3 equivalents of tetrabutylammoniumhydroxide melted by methanol. Then, a main band of the melted solution was separated by Sephadex LH-20 by using methanol as a diluent. The separated solution was added with 0.1M nitric acid to separate the sediment. The sediment was filtered by filter paper and then dried to create DCSC-13. 1H NMR (DMSO): 9.38 (d, 1H), 9.17 (d, 1H), 9.05 (s, 1H), 8.90 (s, 1H), 8.86 (s, 1H), 8.71 (s, 1H), 8.26 (d, 1H), 8.05 (d, 1H), 7.8~6.8 (m, 20H), 4.04 (m, 16H), 2.17 (s, 3H), 2.15 (s, 3H), 1.84 (m, 8H), 1.67 (m, 16H), 0.96 (m, 48H). Anal. Calcd. for C$_{98}$H$_{124}$N$_6$O$_{12}$RuS$_2$: C, 67.52; H, 7.17; N, 4.82 Found: C, 67.38; H, 7.10; N, 4.75 i. [Ru(II)LL''(NCS)$_2$] (L=OPV ligand, L''=4,4'-bis(carboxyvinyl)-2,2'-bipyridine$^2$), DCSC-14

A No. 7 compound (0.19 g, 0.15 mmol) as OPV ligand and dichloro(p-cymene)Ruthenium(II) dimmer (0.044 g, 0.073 mmol) were added with a DMF solvent and agitated at 80° C. for 4 hours. 4,4'-bis(carboxyvinyl)-2,2'-bipyridine (0.043 g, 0.15 mmol) was added to the mixture and agitated at 160° C. for another 4 hours. Then, ammonium thiocyanate (0.17 g, 2.18 mmol) was added to the mixture and agitated at 130° C. for 4 hours, and the solvent was removed in a vacuum. Water of 200 mL was added to form sediment and then the mixture was filtered. The filtered solid was dried and then melted by 3 equivalents of tetrabutylammoniumhydroxide melted by methanol. Then, a main band of the melted solution was separated by Sephadex LH-20 by using methanol as a diluent. The separated solution was added with 0.1 M nitric acid to separate the sediment. The sediment was filtered by filter paper and then dried to create DCSC-14. 1H NMR (DMSO): 9.25 (d, 1H), 9.15 (d, 1H), 8.98 (s, 1H), 8.83 (s, 1H), 8.68 (s, 1H), 8.18 (s, 1H), 8.1~6.8 (m, 26H), 3.99 (m, 16H), 2.16 (s, 3H), 2.15 (s, 3H), 1.81 (m, 8H), 1.67 (m, 16H), 0.95 (m, 48H). Anal. Calcd. for C$_{102}$H$_{128}$N$_6$O$_{12}$RuS$_2$: C, 68.24H, 7.19; N, 4.68. Found: C, 68.11; H, 7.17; N, 4.65.

[Exemplary Embodiment 2] Fabrication of Solar Cell

The solar cell was manufactured by using a TiO$_2$ film formed by Dyesol titania paste (Dyesol Ltd., Australia). The Dyesol paste was coated on an FTO glass substrate which is prior-treated with titaniumtetrachloride, with doctor blade. The paste coated on the FTO glass substrate is fired at 450° C. for 30 minutes to form a TiO$_2$ film having a thickness of 2 μm. The fired thin film was dipped into a dye solution at normal temperatures for 18 hours. The dye solution was made by dissolving the dye DCSC 13 manufactured according to the exemplary embodiment 1 with a concentration of 0.3 mM by a solvent. The solvent includes acetonitrile and tert-butylalcohol at a volume ratio of 1:1. The dye-coated thin film was dipped into the solvent for 3 hours to remove unbonded dye. Then, the thin film was dipped into an ethanol solution for 3 days to remove DMF therefrom. The dye-coated TiO$_2$ film was cleansed with ethanol and then the solar cell was manufactured by a typical solar cell manufacturing method.

The redox electrolyte solution which is used in the solar cell includes a solvent formed by mixing valeronitrile and acetonitrile at a volume ratio of 15:85. 0.6 M M-methyl-N-butyl imidazolium iodine, 0.04 M iodine, 0.025 M LiI, 0.05 M guanidinium thiocyanate and 0.28 M tert-butylpyridine were dissolved to be used.

[Exemplary Embodiments 3 to 5 and Comparative Embodiments 1 and 2]

A solar cell was manufactured according to the same method as that of the exemplary embodiment 2, except that the dye DCSC13 was replaced by a dye DCSC14 (exemplary embodiment 4), a following compound (exemplary embodiments 4 and 5), N820 and N945.

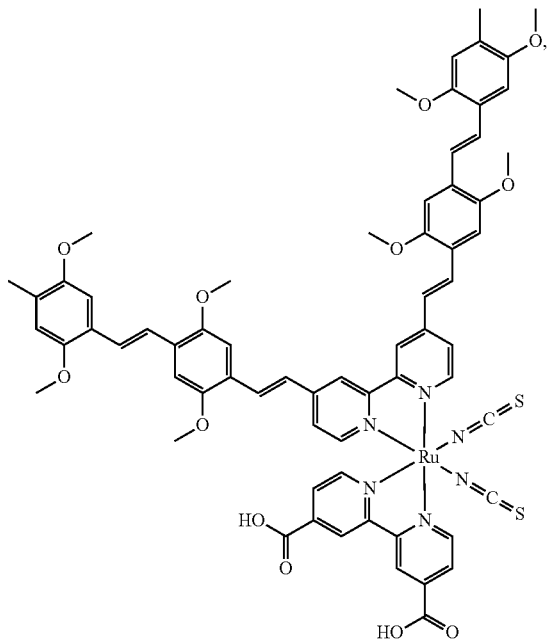

-continued

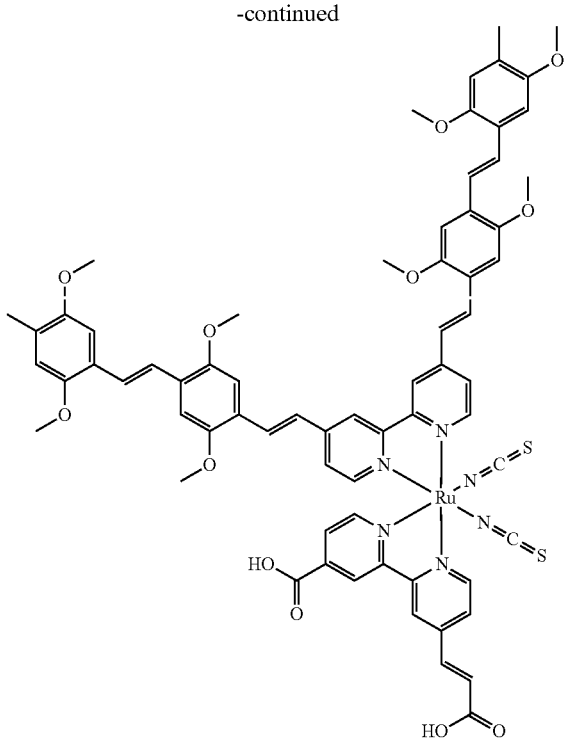

According to analysis of the amount of the dye absorbed to the TiO$_2$ film, the dyes DCSC 13 and DCSC 14 were absorbed as much as 40 M % of N820 and 80 M % of N945.

The molar extinction coefficient, absorbance spectrum and photoelectrochemical characteristics, IPCE index and electron lifetime of the manufactured solar cells are measured and shown in Table 1, FIG. 1, Table 2, FIGS. 2 and 3.

Table 1 shows a absorbance peak and a molar extinction coefficient of the dye solutions which are formed by dissolving the dyes DCSC13, N820 and N945 manufactured according to the exemplary embodiment 1 to have a concentration of 0.3 mM The solvent used includes acetonitrile and tert-butylalcohol at a volume ratio of 1:1. FIGS. 1, 2 and 3 illustrate absorbance spectrum, IPCE (incident photon-to-current conversion efficiency) indices and electron lifetime according to voltage differences of the solar cell of which the TiO$_2$ film has a thinner thickness of 2 μm than 15 μm to 20 μm of a conventional TiO$_2$ film. Table 2 illustrates $J_{sc}$ (short-circuit photocurrent density), $V_{oc}$ (open circuit voltage), FF (fill factor) and photoelectric conversion efficiency (ii).

The photoelectrochemical characteristics of the solar cell were measured with Keithley M 236 source measuring device. The light source includes a 300 W Xe lamp having an AM 1.5 filter (Oriel). The size of the electrode was 0.4×0.4 cm$^2$ and intensity of light was 1 sun (100 mW/cm$^2$). The intensity of light was adjusted with a Si solar cell. The IPCE indices were measured with a system of PV Measurement Co. The absorbance spectrum of the dye in the solution and the TiO$_2$ layer was measured with HP 8453A diode array spectrophotometer.

TABLE 1

| Dye | ϵ(M−1 cm−1(wavelength) | |
|---|---|---|
| N820 | 11300(383) | 11600(524) |
| N945 | 34500(400) | 18900(550) |
| DCSC13 | 72040(442) | 30580(554) |

TABLE 2

| Dye | $J_{sc}$ (mA/cm$^2$) | $V_{oc}$ (mV) | FF | η (%) |
|---|---|---|---|---|
| N820 | 9.900 | 691 | 0.719 | 4.47 |
| DCSC13 | 10.03 | 733 | 0.682 | 50.1 |

As shown in Table 1, the dye DCSC13 according to the exemplary embodiment of the present invention has a higher molar extinction coefficient than the conventional dyes N820 and N945 do. As shown in FIG. 1, the dye according to the present invention has a higher or equivalent absorbance spectrum than the conventional dyes do even through it has a small amount of absorbance. As shown therein, the dye according to the present invention is shifted to the red part of the spectrum.

The solar cell which is manufactured according to the exemplary embodiment 2 and the comparative embodiment 1 with the DCSC13 has better photoelectrochemical characteristics (refer to Table 2), IPCE index (refer to FIG. 2) and electron lifetime (refer to FIG. 3) than the solar cell including the dye N820 does. That is, the dye and oxide semiconductor particles which are used to manufacture the solar cell according to the present invention provide good efficiency even through a small amount of them is used.

The solar cells according to the exemplary embodiments 3 to 5 which use the dye according to the present invention provide results similar to those of the solar cell using the dye DCSC13, and provide better molar extinction coefficient, absorbance spectrum, photoelectrochemical characteristics, IPCE index and electron lifetime than the conventional dyes such as N820.

Although a few exemplary embodiments of the present invention have been shown and described, it will be appreciated by those skilled in the art that changes may be made in these exemplary embodiments without departing from the principles and spirit of the invention, the scope of which is defined in the appended claims and their equivalents.

Industrial Applicability

As described above, the present invention provides a ruthenium-type dye which improves a molar extinction coefficient to enhance efficiency of a solar cell with only a small amount of a dye and oxide semiconductor particles, allows a thin film solar cell element to be manufactured without difficulty and sharply reduces manufacturing costs of a solar cell.

15. The ruthenium-type sensitizer according to claim 1, wherein the sensitizer comprises the following compound:
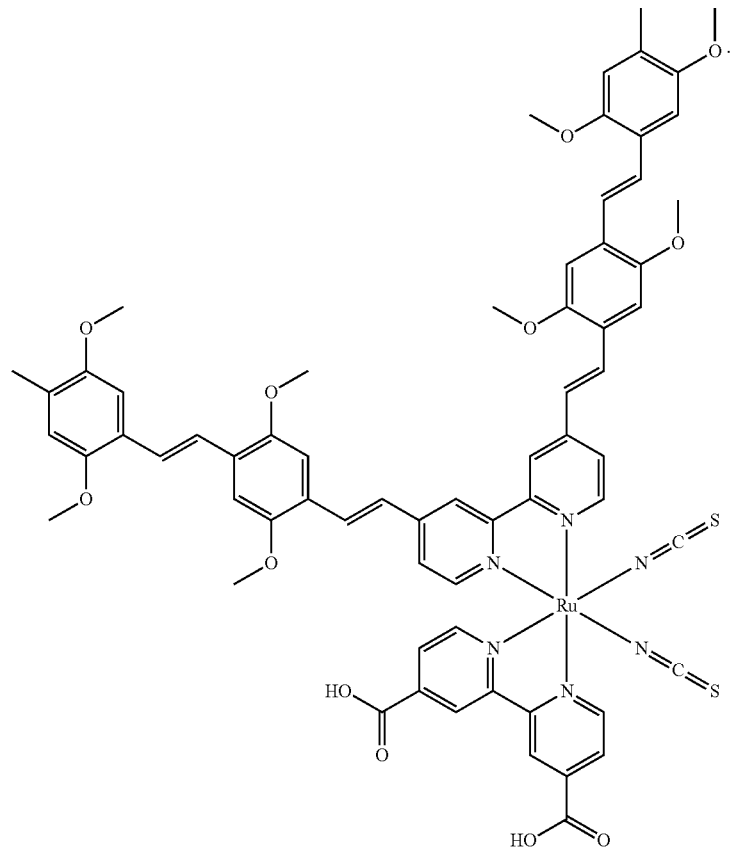

16. The ruthenium-type sensitizer which comprises the following compound:
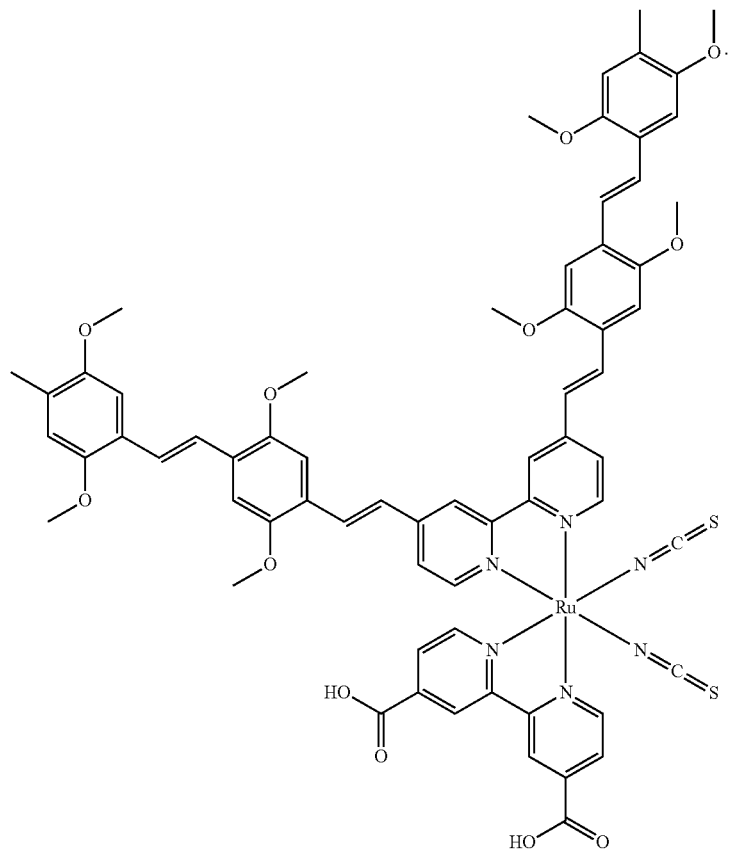

The invention claimed is:
1. A ruthenium-type sensitizer which is represented by a following chemical formula 1, comprising:

[Chemical formula 1]

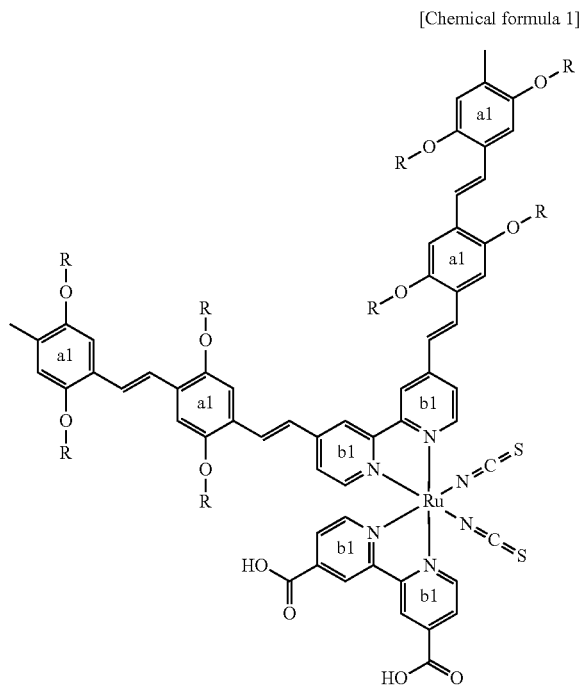

wherein:

ring a1 does not include any substituent or includes at least one substituent at a position of a hydrogen atom, the at least one substituent comprising a halogen atom, an amide group, a cyano group, a hydroxyl group, a nitro group, an alkoxyl group or an acyl group;

ring b1 does not include any substituent or includes at least one substituent at a position of a hydrogen atom, the at least one substituent comprising a halogen atom, an amide group, a cyano group, a hydroxyl group, a nitro group, an alkoxyl group or an acyl group; and R is the same or different and each R independently includes a saturated or unsaturated alkyl group having 1 to 30 carbons which does not include any substituent or includes at least one substituent, the at least one substituent comprising a halogen atom, an amide group, a cyano group, a hydroxyl group, a nitro group, an alkoxyl group or an acyl group.

2. A ruthenium-type sensitizer which is represented by a following chemical formula 2, comprising:

[Chemical formula 2]

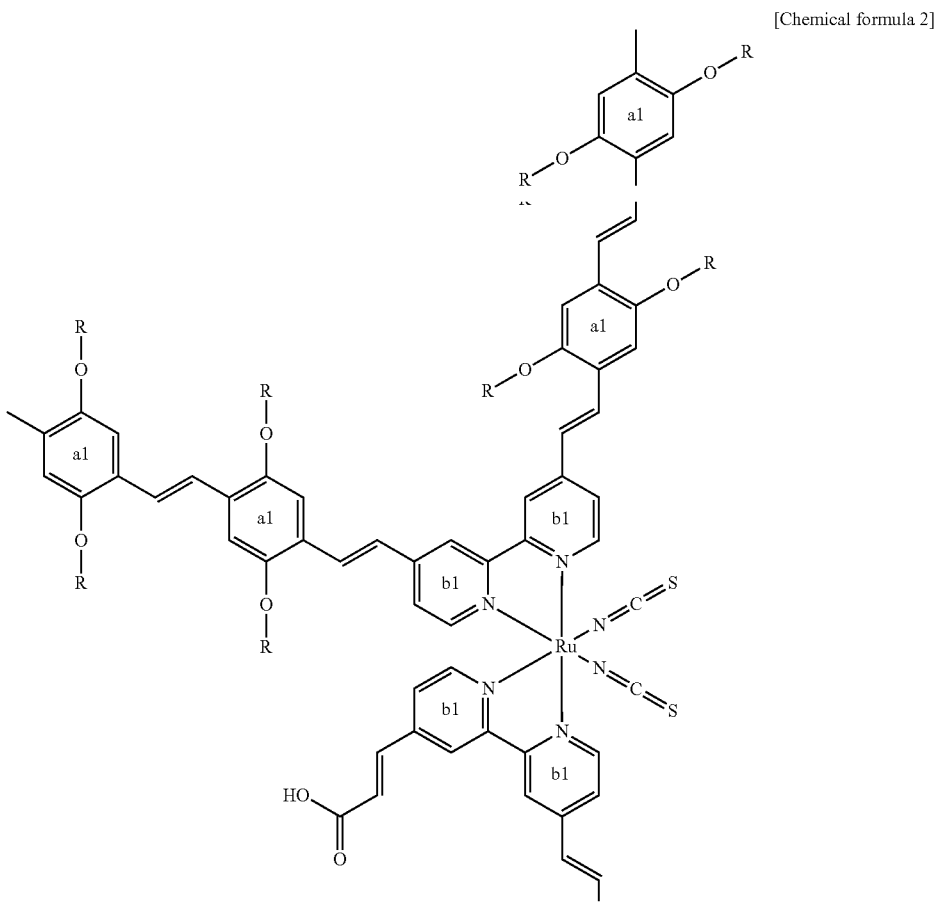

-continued

[Structure: HOOC group]

wherein;

ring a1 does not include any substituent or includes at least one substituent at a position of a hydrogen atom, the at least one substituent comprising a halogen atom, an amide group, a cyano group, a hydroxyl group, a nitro group, an alkoxyl group or an acyl group;

ring b1 does not include any substituent or includes at least one substituent at a position of a hydrogen atom, the at least one substituent comprising a halogen atom, an amide group, a cyano group, a hydroxyl group, a nitro group, an alkoxyl group or an acyl group; and R is the same or different and each R independently includes a saturated or unsaturated alkyl group having 1 to 30 carbons which does not include any substituent or includes at least one substituent, the at least one substituent comprising a halogen atom, an amide group, a cyano group, a hydroxyl group, a nitro group, an alkoxyl group or an acyl group.

3. The ruthenium-type sensitizer according to claim 1, wherein R in the chemical formula 1 comprises saturated alkyl having 1 to 5 carbons, independently.

4. A method of preparing a ruthenium-type sensitizer represented by chemical formula 1, the method comprising sequentially reacting a compound of chemical formula 4 with compounds of chemical formulas 3, 5 and 6, wherein:

[Chemical formula 1]

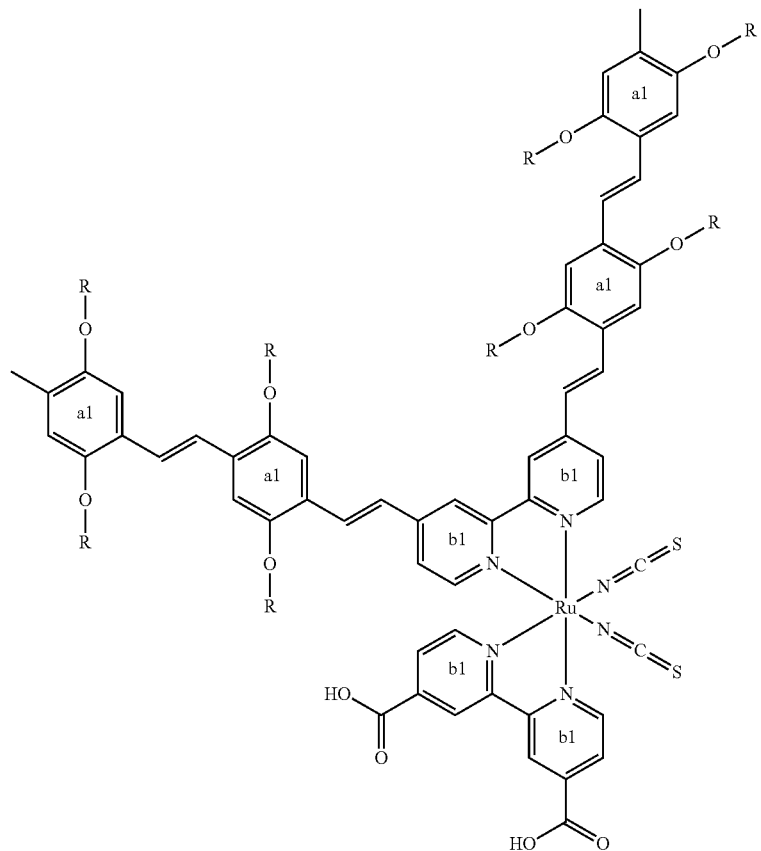

[Chemical formula 3]

[RuCl$_2$ (p-cymene)]$_2$

[Chemical formula 4]

-continued

[Chemical formula 5]

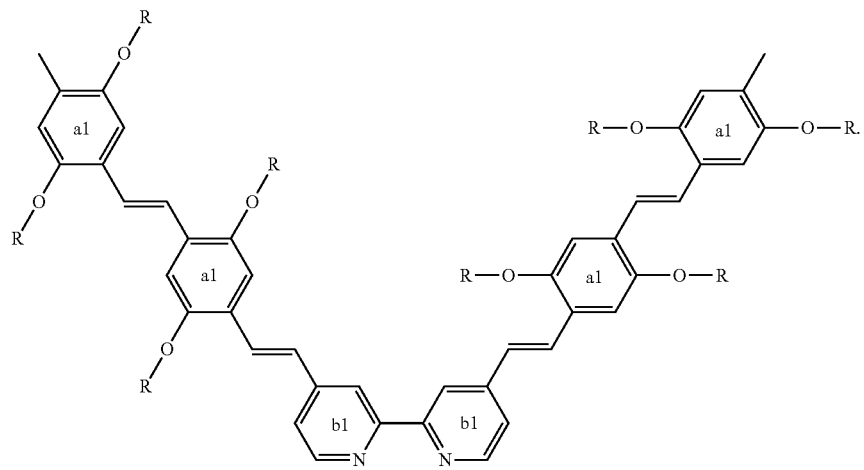

[Chemical formula 6]

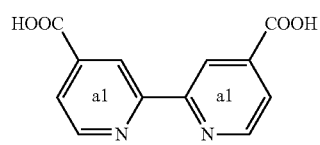

NH₄NCS where:

ring a1 does not include any substituent or includes at least one substituent at a position of a hydrogen atom, the at least one substituent comprising a halogen atom, an amide group, a cyano group, a hydroxyl group, a nitro group, an alkoxyl group or an acyl group;

ring b1 does not include any substituent or includes at least one substituent at a position of a hydrogen atom, the at least one substituent comprising a halogen atom, an amide group, a cyano group, a hydroxyl group, a nitro group, an alkoxyl group or an acyl group; and R is the same or different and each R independently includes a saturated or unsaturated alkyl group having 1 to 30 carbons which does not include any substituent or includes at least one substituent, the at least one substituent comprising a halogen atom, an amide group, a cyano group, a hydroxyl group, a nitro group, an alkoxyl group or an acyl group.

5. A method of preparing a ruthenium-type sensitizer represented by chemical formula 2, the method comprising sequentially reacting a compound of chemical formula 4 with compounds of chemical formulas 3, 6 and 7, the wherein:

[Chemical formula 2]
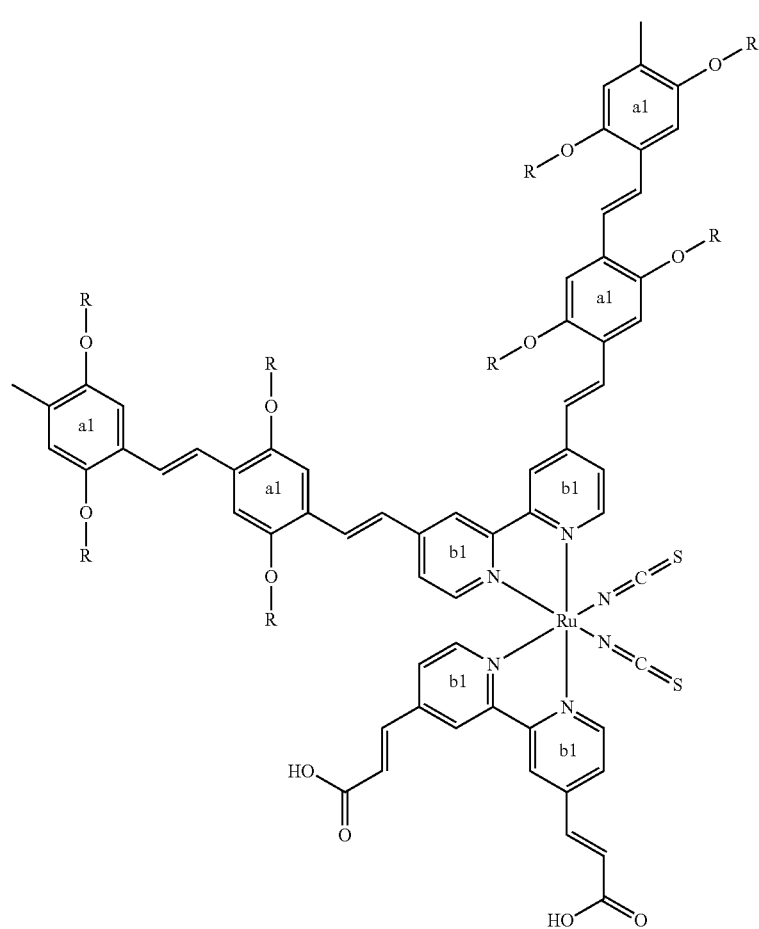
[RuCl₂ (p-cymene)]₂
[Chemical formula 3]
[Chemical formula 4]
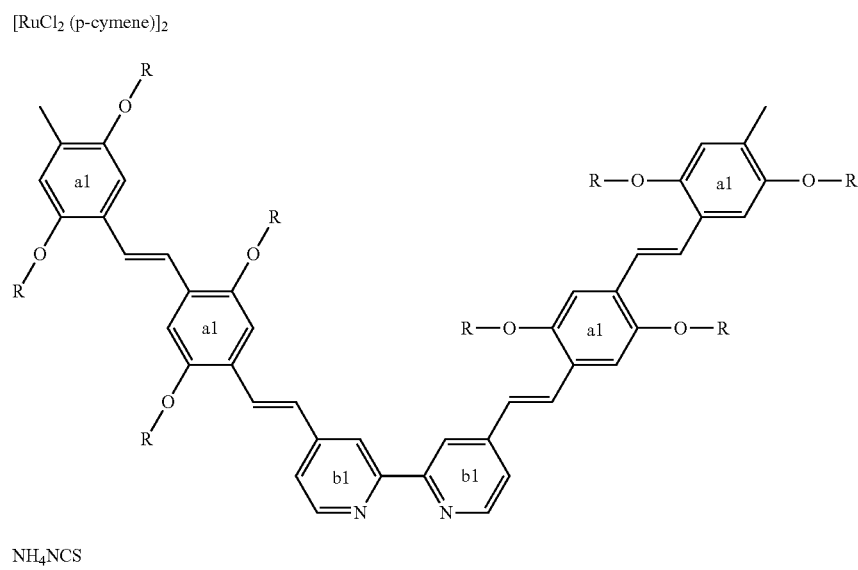
NH₄NCS
[Chemical formula 6]
[Chemical formula 7]
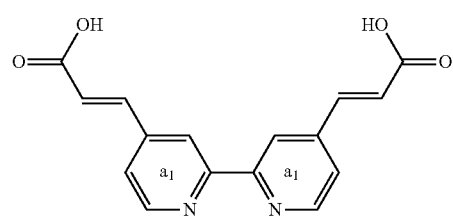

where:
ring a1 does not include any substituent or includes at least one substituent at a position of a hydrogen atom, the at least one substituent comprising a halogen atom, an amide group, a cyano group, a hydroxyl group, a nitro group, an alkoxyl group or an acyl group;

ring b1 does not include any substituent or includes at least one substituent at a position of a hydrogen atom, the at least one substituent comprising a halogen atom, an amide group, a cyano group, a hydroxyl group, a nitro group, an alkoxyl group or an acyl group; and R is the same or different and each R independently includes a saturated or unsaturated alkyl group having 1 to 30 carbons which does not include any substituent or includes at least one substituent, the at least one substituent comprising a halogen atom, an amide group, a cyano group, a hydroxyl group, a nitro group, an alkoxyl group or an acyl group.

6. A dye-sensitized photoelectric conversion element which comprises oxide semiconductor particles having the sensitizer according to claim 1.

7. The dye-sensitized photoelectric conversion element according to claim 6, wherein the oxide semiconductor particles are dipped into the dye under a presence of an inclusion compound.

8. The dye-sensitized photoelectric conversion element according to claim 6, wherein the oxide semiconductor particles comprise titanium dioxide as an essential component.

9. A dye-sensitized solar cell which comprises the dye-sensitized photoelectric conversion element according to claim 6.

10. The dye-sensitized solar cell according to claim 9, wherein the dye-sensitized solar cell is manufactured by an operation of coating a titanium dioxide paste on a transparent conductive substrate, an operation of firing the paste-coated substrate to form a $TiO_2$ layer thereon, an operation of applying a mixture having the dissolved dye represented by the chemical formula 1 or 2 to the substrate having the $TiO_2$ layer to form a $TiO_2$ film electrode having the dye, an operation of providing a second glass substrate having a counter electrode thereon, an operation of forming a hole passing through the second glass substrate and the counter electrode, an operation of coupling the counter electrode and the $TiO_2$ film electrode by heat and press, leaving a thermoplastic polymer film between the counter electrode and the $TiO_2$ film electrode having the dye, an operation of injecting an electrolyte to the thermoplastic polymer film interposed between the counter electrode and the $TiO_2$ film electrode through the hole and an operation of sealing the thermoplastic polymer film.

11. The ruthenium-type sensitizer according to claim 2, wherein R in the chemical formula 2 comprises saturated alkyl having 1 to 5 carbons, independently.

12. A dye-sensitized photoelectric conversion element which comprises oxide semiconductor particles having the sensitizer according to claim 2.

13. The ruthenium-type sensitizer according to claim 1, wherein the sensitizer comprises the following compound:

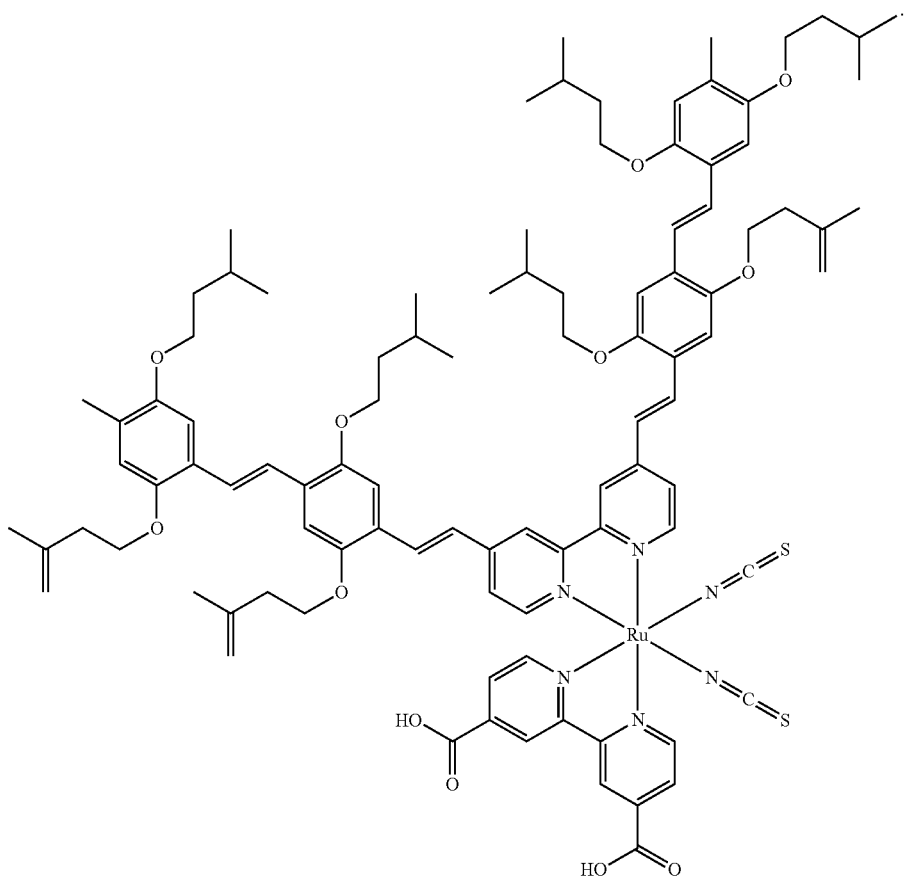

14. The ruthenium-type sensitizer according to claim 2, wherein the sensitizer comprises the following compound:
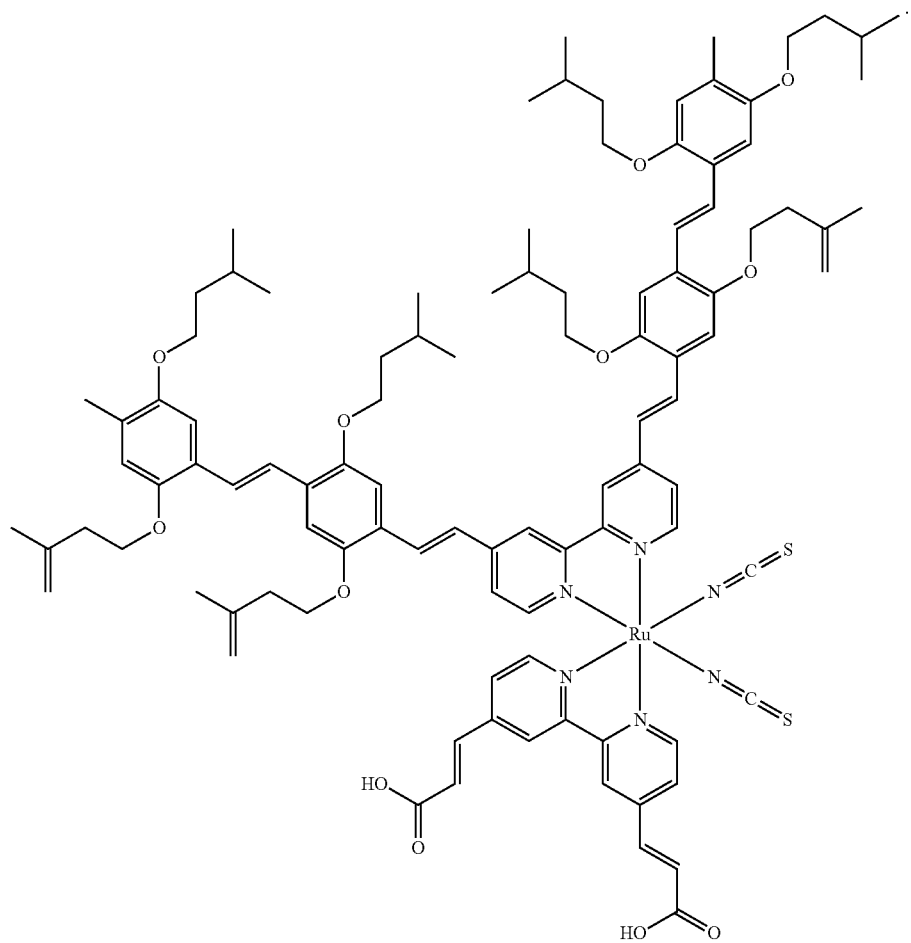
DCSC 14